US012653949B2

(12) United States Patent
Narayanaswami

(10) Patent No.: US 12,653,949 B2
(45) Date of Patent: Jun. 16, 2026

(54) ADAPTATION OF MEDICAMENT DELIVERY IN RESPONSE TO USER STRESS LOAD

(71) Applicant: INSULET CORPORATION, Acton, MA (US)

(72) Inventor: Rangarajan Narayanaswami, Weston, MA (US)

(73) Assignee: INSULET CORPORATION, Acton, MA (US)

( * ) Notice: Subject to any disclaimer, the term of this patent is extended or adjusted under 35 U.S.C. 154(b) by 1006 days.

(21) Appl. No.: 17/812,817

(22) Filed: Jul. 15, 2022

(65) Prior Publication Data

US 2023/0032033 A1 Feb. 2, 2023

Related U.S. Application Data

(60) Provisional application No. 63/227,275, filed on Jul. 29, 2021.

(51) Int. Cl.
*A61M 5/172* (2006.01)

(52) U.S. Cl.
CPC ....... *A61M 5/1723* (2013.01); *A61M 2230/06* (2013.01); *A61M 2230/50* (2013.01); *A61M 2230/63* (2013.01); *A61M 2230/65* (2013.01)

(58) Field of Classification Search
None
See application file for complete search history.

(56) References Cited

U.S. PATENT DOCUMENTS

| 303,013 | A | 8/1884 | Horton |
| 441,663 | A | 12/1890 | Hofbauer |
| 445,545 | A | 2/1891 | Crane |

(Continued)

FOREIGN PATENT DOCUMENTS

| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Manuel A Mendez
(74) *Attorney, Agent, or Firm* — Goodwin Procter LLP

(57) ABSTRACT

Disclosed are an automatic medication delivery system includes a stress detection and response algorithm or application that may operate in cooperation with a medication delivery algorithm or application. Execution of the instructions of the stress detection and response application causes a processor to obtain a respective measurement value related to a physiological condition of a user from one or more sensors. The obtained respective measurement values are evaluated against a respective threshold measurement value. The processor determines, based on the evaluation of the obtained respective measurement values, a degree of stress the user is experiencing. In response to the determination of the degree of stress the user is experiencing, the processor may modify an imminent dosage of a liquid drug to be delivered, a time of delivery of the imminent dosage, or both. A dosage of the liquid drug may be expelled based on the modifying.

20 Claims, 16 Drawing Sheets

(56) References Cited

U.S. PATENT DOCUMENTS

| | | | |
|---|---|---|---|
| 588,583 A | 8/1897 | Lade | |
| 955,911 A | 4/1910 | Saegmuller | |
| 1,441,508 A | 1/1923 | Marius | |
| 2,283,925 A | 5/1942 | Harvey | |
| 2,797,149 A | 6/1957 | Skeggs | |
| 2,886,529 A | 5/1959 | Guillaud | |
| 3,574,114 A | 4/1971 | Monforte | |
| 3,614,554 A | 10/1971 | Shield | |
| 3,631,847 A | 1/1972 | Hobbs | |
| 3,634,039 A | 1/1972 | Brondy | |
| 3,812,843 A | 5/1974 | Wootten et al. | |
| 3,841,328 A | 10/1974 | Jensen | |
| 3,870,034 A * | 3/1975 | James | A61B 5/486 |
| | | | 324/692 |
| 3,885,662 A | 5/1975 | Schaefer | |
| 3,963,380 A | 6/1976 | Thomas, Jr. et al. | |
| 3,983,077 A | 9/1976 | Fuller et al. | |
| 4,055,175 A | 10/1977 | Clemens et al. | |
| 4,108,177 A | 8/1978 | Pistor | |
| 4,146,029 A | 3/1979 | Ellinwood, Jr. | |
| 4,151,845 A | 5/1979 | Clemens | |
| 4,206,401 A | 6/1980 | Meyer | |
| 4,245,634 A | 1/1981 | Albisser et al. | |
| 4,268,150 A | 5/1981 | Chen | |
| 4,277,226 A | 7/1981 | Archibald | |
| 4,307,713 A | 12/1981 | Galkin et al. | |
| 4,313,439 A | 2/1982 | Babb et al. | |
| 4,368,980 A | 1/1983 | Aldred et al. | |
| 4,373,527 A | 2/1983 | Fischell | |
| 4,398,542 A | 8/1983 | Cunningham et al. | |
| 4,400,683 A | 8/1983 | Eda et al. | |
| 4,403,984 A | 9/1983 | Ash et al. | |
| 4,424,720 A | 1/1984 | Bucchianeri | |
| 4,435,173 A | 3/1984 | Siposs et al. | |
| 4,464,170 A | 8/1984 | Clemens et al. | |
| 4,469,481 A | 9/1984 | Kobayashi | |
| 4,475,901 A | 10/1984 | Kraegen et al. | |
| 4,498,843 A | 2/1985 | Schneider et al. | |
| 4,507,115 A | 3/1985 | Kambara et al. | |
| 4,523,170 A | 6/1985 | Huth, III | |
| 4,526,568 A | 7/1985 | Clemens et al. | |
| 4,526,569 A | 7/1985 | Bernardi | |
| 4,529,401 A | 7/1985 | Leslie et al. | |
| 4,551,134 A | 11/1985 | Slavik et al. | |
| 4,559,033 A | 12/1985 | Stephen et al. | |
| 4,559,037 A | 12/1985 | Franetzki et al. | |
| 4,560,979 A | 12/1985 | Rosskopf | |
| 4,562,751 A | 1/1986 | Nason et al. | |
| 4,573,968 A | 3/1986 | Parker | |
| 4,585,439 A | 4/1986 | Michel | |
| 4,587,850 A | 5/1986 | Moser | |
| 4,601,707 A | 7/1986 | Albisser et al. | |
| 4,624,661 A | 11/1986 | Arimond | |
| 4,633,878 A | 1/1987 | Bombardieri | |
| 4,634,427 A | 1/1987 | Hannula et al. | |
| 4,646,038 A | 2/1987 | Wanat | |
| 4,657,529 A | 4/1987 | Prince et al. | |
| 4,678,408 A | 7/1987 | Nason et al. | |
| 4,684,368 A | 8/1987 | Kenyon | |
| 4,685,903 A | 8/1987 | Cable et al. | |
| 4,731,726 A | 3/1988 | Allen, III | |
| 4,743,243 A | 5/1988 | Vaillancourt | |
| 4,755,169 A | 7/1988 | Sarnoff et al. | |
| 4,755,173 A | 7/1988 | Konopka et al. | |
| 4,759,120 A | 7/1988 | Bernstein | |
| 4,781,688 A | 11/1988 | Thoma et al. | |
| 4,781,693 A | 11/1988 | Martinez et al. | |
| 4,801,957 A | 1/1989 | Vandemoere | |
| 4,808,161 A | 2/1989 | Kamen | |
| 4,836,752 A | 6/1989 | Burkett | |
| 4,850,954 A | 7/1989 | Charvin | |
| 4,854,170 A | 8/1989 | Brimhall et al. | |
| 4,859,492 A | 8/1989 | Rogers, Jr. et al. | |
| 4,880,770 A | 11/1989 | Mir et al. | |
| 4,882,600 A | 11/1989 | Van de Moere | |
| 4,886,499 A | 12/1989 | Cirelli et al. | |
| 4,898,578 A | 2/1990 | Rubalcaba, Jr. | |
| 4,898,579 A | 2/1990 | Groshong et al. | |
| 4,900,292 A | 2/1990 | Berry et al. | |
| 4,919,596 A | 4/1990 | Slate et al. | |
| 4,925,444 A | 5/1990 | Orkin et al. | |
| 4,940,527 A | 7/1990 | Kazlauskas et al. | |
| 4,944,659 A | 7/1990 | Labbe et al. | |
| 4,961,055 A | 10/1990 | Habib et al. | |
| 4,967,201 A | 10/1990 | Rich, III | |
| 4,969,874 A | 11/1990 | Michel et al. | |
| 4,973,998 A | 11/1990 | Gates | |
| 4,975,581 A | 12/1990 | Robinson et al. | |
| 4,976,720 A | 12/1990 | Machold et al. | |
| 4,981,140 A | 1/1991 | Wyatt | |
| 4,994,047 A | 2/1991 | Walker et al. | |
| 5,007,286 A | 4/1991 | Malcolm et al. | |
| 5,007,458 A | 4/1991 | Marcus et al. | |
| 5,045,871 A | 9/1991 | Reinholdson | |
| 5,062,841 A | 11/1991 | Siegel | |
| 5,084,749 A | 1/1992 | Losee et al. | |
| 5,097,834 A | 3/1992 | Skrabal | |
| 5,102,406 A | 4/1992 | Arnold | |
| 5,109,850 A | 5/1992 | Blanco et al. | |
| 5,125,415 A | 6/1992 | Bell | |
| 5,130,675 A | 7/1992 | Sugawara | |
| 5,134,079 A | 7/1992 | Cusack et al. | |
| 5,139,999 A | 8/1992 | Gordon et al. | |
| 5,153,827 A | 10/1992 | Coutre et al. | |
| 5,154,973 A | 10/1992 | Imagawa et al. | |
| 5,165,406 A | 11/1992 | Wong | |
| 5,176,662 A | 1/1993 | Bartholomew et al. | |
| 5,178,609 A | 1/1993 | Ishikawa | |
| 5,189,609 A | 2/1993 | Tivig et al. | |
| 5,198,824 A | 3/1993 | Poradish | |
| 5,205,819 A | 4/1993 | Ross et al. | |
| 5,207,642 A | 5/1993 | Orkin et al. | |
| 5,213,483 A | 5/1993 | Flaherty et al. | |
| 5,217,754 A | 6/1993 | Santiago-Aviles et al. | |
| 5,219,377 A | 6/1993 | Poradish | |
| 5,232,439 A | 8/1993 | Campbell et al. | |
| 5,237,993 A | 8/1993 | Skrabal | |
| 5,239,326 A | 8/1993 | Takai | |
| 5,244,463 A | 9/1993 | Cordner, Jr. et al. | |
| 5,254,096 A | 10/1993 | Rondelet et al. | |
| 5,257,980 A | 11/1993 | Van Antwerp et al. | |
| 5,261,882 A | 11/1993 | Sealfon | |
| 5,263,198 A | 11/1993 | Geddes et al. | |
| 5,272,485 A | 12/1993 | Mason et al. | |
| 5,273,517 A | 12/1993 | Barone et al. | |
| 5,281,202 A | 1/1994 | Weber et al. | |
| 5,281,808 A | 1/1994 | Kunkel | |
| 5,299,571 A | 4/1994 | Mastrototaro | |
| 5,308,982 A | 5/1994 | Ivaldi et al. | |
| 5,342,298 A | 8/1994 | Michaels et al. | |
| 5,346,476 A | 9/1994 | Elson | |
| 5,364,342 A | 11/1994 | Beuchat et al. | |
| 5,377,674 A | 1/1995 | Kuestner | |
| 5,380,665 A | 1/1995 | Cusack et al. | |
| 5,385,539 A | 1/1995 | Maynard | |
| 5,389,078 A | 2/1995 | Zalesky | |
| 5,403,797 A | 4/1995 | Ohtani et al. | |
| 5,411,889 A | 5/1995 | Hoots et al. | |
| 5,421,812 A | 6/1995 | Langley et al. | |
| 5,427,988 A | 6/1995 | Sengupta et al. | |
| 5,433,710 A | 7/1995 | VanAntwerp et al. | |
| 5,452,033 A | 9/1995 | Balling et al. | |
| 5,456,945 A | 10/1995 | McMillan et al. | |
| 5,468,727 A | 11/1995 | Phillips et al. | |
| 5,478,610 A | 12/1995 | Desu et al. | |
| 5,505,709 A | 4/1996 | Funderburk et al. | |
| 5,505,828 A | 4/1996 | Wong et al. | |
| 5,507,288 A | 4/1996 | Bocker et al. | |
| 5,513,382 A | 4/1996 | Agahi-Kesheh et al. | |
| 5,533,389 A | 7/1996 | Kamen et al. | |
| 5,535,445 A | 7/1996 | Gunton | |
| 5,540,772 A | 7/1996 | McMillan et al. | |
| 5,543,773 A | 8/1996 | Evans et al. | |
| 5,558,640 A | 9/1996 | Pfeiler et al. | |

(56)                References Cited

U.S. PATENT DOCUMENTS

| | | |
|---|---|---|
| 5,563,584 A | 10/1996 | Rader et al. |
| 5,569,186 A | 10/1996 | Lord et al. |
| 5,576,781 A | 11/1996 | Deleeuw |
| 5,582,593 A | 12/1996 | Hultman |
| 5,584,053 A | 12/1996 | Kommrusch et al. |
| 5,584,813 A | 12/1996 | Livingston et al. |
| 5,585,733 A | 12/1996 | Paglione |
| 5,586,553 A | 12/1996 | Halili et al. |
| 5,590,387 A | 12/1996 | Schmidt et al. |
| 5,609,572 A | 3/1997 | Lang |
| 5,614,252 A | 3/1997 | McMillan et al. |
| 5,625,365 A | 4/1997 | Tom et al. |
| 5,635,433 A | 6/1997 | Sengupta |
| 5,637,095 A | 6/1997 | Nason et al. |
| 5,647,853 A | 7/1997 | Feldmann et al. |
| 5,660,163 A | 8/1997 | Schulman et al. |
| 5,665,065 A | 9/1997 | Colman et al. |
| 5,665,070 A | 9/1997 | McPhee |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,707,459 A | 1/1998 | Itoyama et al. |
| 5,707,715 A | 1/1998 | deRochemont et al. |
| 5,713,875 A | 2/1998 | Tanner, II |
| 5,714,123 A | 2/1998 | Sohrab |
| 5,716,343 A | 2/1998 | Kriesel et al. |
| 5,722,397 A | 3/1998 | Eppstein |
| 5,726,404 A | 3/1998 | Brody |
| 5,726,751 A | 3/1998 | Altendorf et al. |
| 5,741,228 A | 4/1998 | Lambrecht et al. |
| 5,746,217 A | 5/1998 | Erickson et al. |
| 5,747,350 A | 5/1998 | Sattler |
| 5,747,870 A | 5/1998 | Pedder |
| 5,748,827 A | 5/1998 | Holl et al. |
| 5,755,682 A | 5/1998 | Knudson et al. |
| 5,758,643 A | 6/1998 | Wong et al. |
| 5,759,923 A | 6/1998 | McMillan et al. |
| 5,764,189 A | 6/1998 | Lohninger |
| 5,771,567 A | 6/1998 | Pierce et al. |
| 5,776,103 A | 7/1998 | Kriesel et al. |
| 5,779,676 A | 7/1998 | Kriesel et al. |
| 5,785,681 A | 7/1998 | Indravudh et al. |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,807,075 A | 9/1998 | Jacobsen et al. |
| 5,817,007 A | 10/1998 | Fodgaard et al. |
| 5,820,622 A | 10/1998 | Gross et al. |
| 5,823,951 A | 10/1998 | Messerschmidt |
| 5,830,999 A | 11/1998 | Dunn |
| 5,839,467 A | 11/1998 | Saaski et al. |
| 5,840,020 A | 11/1998 | Heinonen et al. |
| 5,848,991 A | 12/1998 | Gross et al. |
| 5,851,197 A | 12/1998 | Marano et al. |
| 5,854,608 A | 12/1998 | Leisten |
| 5,858,005 A | 1/1999 | Kriesel |
| 5,858,239 A | 1/1999 | Kenley et al. |
| 5,859,621 A | 1/1999 | Leisten |
| 5,865,806 A | 2/1999 | Howell |
| 5,867,688 A | 2/1999 | Simmon et al. |
| 5,871,470 A | 2/1999 | McWha |
| 5,879,310 A | 3/1999 | Sopp et al. |
| 5,889,459 A | 3/1999 | Hattori et al. |
| 5,891,097 A | 4/1999 | Saito et al. |
| 5,892,489 A | 4/1999 | Kanba et al. |
| 5,897,530 A | 4/1999 | Jackson |
| 5,899,882 A | 5/1999 | Waksman et al. |
| 5,902,253 A | 5/1999 | Pfeiffer et al. |
| 5,903,421 A | 5/1999 | Furutani et al. |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,932,175 A | 8/1999 | Knute et al. |
| 5,933,121 A | 8/1999 | Rainhart et al. |
| 5,935,099 A | 8/1999 | Peterson et al. |
| 5,945,963 A | 8/1999 | Leisten |
| 5,947,911 A | 9/1999 | Wong et al. |
| 5,957,890 A | 9/1999 | Mann et al. |
| 5,961,492 A | 10/1999 | Kriesel et al. |
| 5,965,848 A | 10/1999 | Altschul et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,019,747 A | 2/2000 | McPhee |
| 6,023,251 A | 2/2000 | Koo et al. |
| 6,024,539 A | 2/2000 | Blomquist |
| 6,027,826 A | 2/2000 | deRochemont et al. |
| 6,028,568 A | 2/2000 | Asakura et al. |
| 6,031,445 A | 2/2000 | Marty et al. |
| 6,032,059 A | 2/2000 | Henning et al. |
| 6,036,924 A | 3/2000 | Simons et al. |
| 6,040,578 A | 3/2000 | Malin et al. |
| 6,040,805 A | 3/2000 | Huynh et al. |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | de Rochemont et al. |
| 6,154,176 A | 11/2000 | Fathy et al. |
| 6,157,041 A | 12/2000 | Thomas et al. |
| 6,161,028 A | 12/2000 | Braig et al. |
| 6,162,639 A | 12/2000 | Douglas |
| 6,171,264 B1 | 1/2001 | Bader |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,309,370 B1 | 10/2001 | Haim et al. |

(56)         References Cited

U.S. PATENT DOCUMENTS

| | | | |
|---|---|---|---|
| 6,312,888 B1 | 11/2001 | Wong et al. |
| 6,320,547 B1 | 11/2001 | Fathy et al. |
| 6,323,549 B1 | 11/2001 | deRochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,381,029 B1 | 4/2002 | Tipirneni |
| 6,402,689 B1 | 6/2002 | Scarantino et al. |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,605,151 B1 | 8/2003 | Wessels et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,685,452 B2 | 2/2004 | Christiansen et al. |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | deRochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,768,319 B2 | 7/2004 | Wang |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,558 B2 | 12/2004 | Flaherty et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,905,989 B2 | 6/2005 | Ellis et al. |
| 6,906,674 B2 | 6/2005 | McKinzie, III et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,047,637 B2 | 5/2006 | deRochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |

(56) References Cited

U.S. PATENT DOCUMENTS

| | | |
|---|---|---|
| 7,182,726 B2 | 2/2007 | Williams et al. |
| 7,190,988 B2 | 3/2007 | Say et al. |
| 7,204,823 B2 | 4/2007 | Estes et al. |
| 7,230,316 B2 | 6/2007 | Yamazaki et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,073 B2 | 12/2007 | Raynal-Olive et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | de Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,522,124 B2 | 4/2009 | Smith et al. |
| 7,547,281 B2 | 6/2009 | Hayes et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,595,623 B2 | 9/2009 | Bennett |
| 7,608,042 B2 | 10/2009 | Goldberger et al. |
| 7,651,845 B2 | 1/2010 | Doyle, III et al. |
| 7,652,901 B2 | 1/2010 | Kirchmeier et al. |
| 7,680,529 B2 | 3/2010 | Kroll |
| 7,714,794 B2 | 5/2010 | Tavassoli Hozouri |
| 7,734,323 B2 | 6/2010 | Blomquist et al. |
| 7,763,917 B2 | 7/2010 | de Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,812,774 B2 | 10/2010 | Friman et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,056,719 B2 | 11/2011 | Porret et al. |
| 8,066,805 B2 | 11/2011 | Zurcher et al. |
| 8,069,690 B2 | 12/2011 | DeSantolo et al. |
| 8,105,282 B2 | 1/2012 | Susi et al. |
| 8,114,489 B2 | 2/2012 | Nemat-Nasser et al. |
| 8,178,457 B2 | 5/2012 | de Rochemont |
| 8,193,873 B2 | 6/2012 | Kato et al. |
| 8,221,345 B2 | 7/2012 | Blomquist |
| 8,251,907 B2 | 8/2012 | Sterling et al. |
| 8,267,921 B2 | 9/2012 | Yodfat et al. |
| 8,285,487 B2 | 10/2012 | Bergstrom et al. |
| 8,348,884 B2 * | 1/2013 | Hildebrand ........... A61M 5/142 |
| | | 604/67 |
| 8,350,657 B2 | 1/2013 | deRochemont |
| 8,354,294 B2 | 1/2013 | de Rochemont et al. |
| 8,449,524 B2 | 5/2013 | Braig et al. |
| 8,452,359 B2 | 5/2013 | Rebec et al. |
| 8,454,557 B1 | 6/2013 | Qi et al. |
| 8,454,576 B2 | 6/2013 | Mastrototaro et al. |
| 8,461,561 B2 | 6/2013 | Freeman et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,593,819 B2 | 11/2013 | de Rochemont |
| 8,597,274 B2 | 12/2013 | Sloan et al. |
| 8,622,988 B2 | 1/2014 | Hayter |
| 8,715,839 B2 | 5/2014 | de Rochemont |
| 8,727,117 B2 | 5/2014 | Maasarani |
| 8,810,394 B2 | 8/2014 | Kalpin |
| 8,939,935 B2 | 1/2015 | OConnor et al. |
| 9,005,166 B2 | 4/2015 | Uber, III et al. |
| 9,061,097 B2 | 6/2015 | Holt et al. |
| 9,171,343 B1 | 10/2015 | Fischell et al. |
| 9,180,244 B2 | 11/2015 | Anderson et al. |
| 9,192,716 B2 | 11/2015 | Jugl et al. |
| 9,233,204 B2 | 1/2016 | Booth et al. |
| 9,248,229 B2 | 2/2016 | Devouassoux et al. |
| 9,402,950 B2 | 8/2016 | Dilanni et al. |
| 9,427,710 B2 | 8/2016 | Jansen |
| 9,486,571 B2 | 11/2016 | Rosinko |
| 9,520,649 B2 | 12/2016 | de Rochemont |
| 9,532,747 B2 * | 1/2017 | LaBelle ................. A61B 5/681 |
| 9,579,456 B2 | 2/2017 | Budiman et al. |
| 9,598,195 B2 | 3/2017 | Deutschle et al. |
| 9,656,017 B2 | 5/2017 | Greene |
| 9,743,224 B2 | 8/2017 | San Vicente et al. |
| 9,857,090 B2 | 1/2018 | Golden et al. |
| 9,862,519 B2 | 1/2018 | Deutschle et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,046,114 B1 | 8/2018 | Biederman et al. |
| 10,086,131 B2 | 10/2018 | Okihara |
| 10,248,839 B2 | 4/2019 | Levy et al. |
| 10,335,464 B1 | 7/2019 | Michelich et al. |
| 10,342,926 B2 | 7/2019 | Nazzaro et al. |
| 10,441,717 B2 | 10/2019 | Schmid et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0032374 A1 | 3/2002 | Holker et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0161307 A1 | 10/2002 | Yu et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0034124 A1 | 2/2003 | Sugaya et al. |
| 2003/0040715 A1 | 2/2003 | DAntonio et al. |
| 2003/0050621 A1 | 3/2003 | Lebel et al. |
| 2003/0060692 A1 | 3/2003 | Ruchti et al. |
| 2003/0073952 A1 | 4/2003 | Flaherty et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0122647 A1 | 7/2003 | Ou |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0170436 A1 | 9/2003 | Sumi et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |

(56) References Cited

U.S. PATENT DOCUMENTS

| | | |
|---|---|---|
| 2003/0220605 A1 | 11/2003 | Bowman, Jr. et al. |
| 2003/0221621 A1 | 12/2003 | Pokharna et al. |
| 2004/0010207 A1 | 1/2004 | Flaherty et al. |
| 2004/0010507 A1 | 1/2004 | Bellew |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Couvillon, Jr. et al. |
| 2004/0069044 A1 | 4/2004 | Lavi et al. |
| 2004/0085215 A1 | 5/2004 | Moberg et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0055242 A1 | 3/2005 | Bello et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0262451 A1 | 11/2005 | Remignanti et al. |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0041229 A1 | 2/2006 | Garibotto et al. |
| 2006/0079765 A1 | 4/2006 | Neer et al. |
| 2006/0079809 A1 | 4/2006 | Goldberger et al. |
| 2006/0086909 A1 | 4/2006 | Schaber |
| 2006/0086994 A1 | 4/2006 | Viefers et al. |
| 2006/0092569 A1 | 5/2006 | Che et al. |
| 2006/0100494 A1 | 5/2006 | Kroll |
| 2006/0134323 A1 | 6/2006 | OBrien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0264926 A1 | 11/2006 | Kochamba |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0027370 A1 | 2/2007 | Brauker et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0078784 A1 | 4/2007 | Donovan et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0166453 A1 | 7/2007 | Van Duren et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0179885 A1 | 8/2007 | Bird et al. |
| 2007/0191716 A1 | 8/2007 | Goldberger et al. |
| 2007/0191770 A1 | 8/2007 | Moberg et al. |
| 2007/0197163 A1 | 8/2007 | Robertson |
| 2007/0225675 A1 | 9/2007 | Robinson et al. |
| 2007/0233051 A1 | 10/2007 | Hohl et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0004515 A1 | 1/2008 | Jennewine |
| 2008/0027371 A1 | 1/2008 | Higuchi et al. |
| 2008/0033272 A1 | 2/2008 | Gough et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0077081 A1 | 3/2008 | Mounce et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0173073 A1 | 7/2008 | Downie et al. |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0255438 A1 | 10/2008 | Saidara et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0281290 A1 | 11/2008 | Yodfat et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0048556 A1 | 2/2009 | Durand |
| 2009/0054753 A1 | 2/2009 | Robinson et al. |
| 2009/0062767 A1 | 3/2009 | Van Antwerp et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0112769 A1 | 4/2009 | Dicks et al. |
| 2009/0131861 A1 | 5/2009 | Braig et al. |
| 2009/0156922 A1 | 6/2009 | Goldberger et al. |
| 2009/0156924 A1 | 6/2009 | Shariati et al. |

(56) References Cited

U.S. PATENT DOCUMENTS

| | | |
|---|---|---|
| 2009/0163781 A1 | 6/2009 | Say et al. |
| 2009/0177142 A1 | 7/2009 | Blomquist et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0254041 A1 | 10/2009 | Krag et al. |
| 2009/0318791 A1 | 12/2009 | Kaastrup |
| 2009/0326343 A1 | 12/2009 | Gable et al. |
| 2009/0326472 A1 | 12/2009 | Carter |
| 2010/0017141 A1 | 1/2010 | Campbell et al. |
| 2010/0036326 A1 | 2/2010 | Matusch |
| 2010/0057042 A1 | 3/2010 | Hayter |
| 2010/0063438 A1* | 3/2010 | Bengtsson .......... A61M 5/1723 |
| | | 340/691.4 |
| 2010/0064243 A1 | 3/2010 | Buck et al. |
| 2010/0076275 A1 | 3/2010 | Chu et al. |
| 2010/0077198 A1 | 3/2010 | Buck et al. |
| 2010/0094251 A1 | 4/2010 | Estes |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0185175 A1 | 7/2010 | Kamen et al. |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0286997 A1 | 11/2010 | Srinivasan |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0049394 A1 | 3/2011 | de Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0124996 A1 | 5/2011 | Reinke et al. |
| 2011/0142688 A1 | 6/2011 | Chappel et al. |
| 2011/0144586 A1 | 6/2011 | Michaud et al. |
| 2011/0152658 A1 | 6/2011 | Peyser et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0213306 A1 | 9/2011 | Hanson et al. |
| 2011/0218495 A1 | 9/2011 | Remebe |
| 2011/0225024 A1 | 9/2011 | Seyer et al. |
| 2011/0230833 A1 | 9/2011 | Landman et al. |
| 2011/0246235 A1 | 10/2011 | Powell et al. |
| 2011/0251509 A1 | 10/2011 | Beyhan et al. |
| 2011/0313680 A1 | 12/2011 | Doyle, III |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0029941 A1 | 2/2012 | Malave et al. |
| 2012/0030393 A1 | 2/2012 | Ganesh et al. |
| 2012/0050046 A1 | 3/2012 | Satorius et al. |
| 2012/0053556 A1 | 3/2012 | Lee |
| 2012/0054841 A1 | 3/2012 | Schultz et al. |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0153936 A1 | 6/2012 | Romani et al. |
| 2012/0182939 A1 | 7/2012 | Rajan et al. |
| 2012/0184909 A1 | 7/2012 | Gyrn |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0250449 A1 | 10/2012 | Nakano |
| 2012/0265166 A1 | 10/2012 | Yodfat |
| 2012/0271655 A1 | 10/2012 | Knobel et al. |
| 2012/0277667 A1 | 11/2012 | Yodat et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0030841 A1 | 1/2013 | Bergstrom et al. |
| 2013/0036100 A1 | 2/2013 | Nagpal et al. |
| 2013/0060194 A1 | 3/2013 | Rostein |
| 2013/0080832 A1 | 3/2013 | Dean et al. |
| 2013/0138452 A1 | 5/2013 | Cork et al. |
| 2013/0158503 A1 | 6/2013 | Kanderian, Jr. et al. |
| 2013/0172695 A1 | 7/2013 | Nielsen et al. |
| 2013/0172710 A1 | 7/2013 | Mears et al. |
| 2013/0173473 A1 | 7/2013 | Birtwhistle et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0274576 A1 | 10/2013 | Amirouche et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | OConnor et al. |
| 2013/0346858 A1 | 12/2013 | Neyrinck |
| 2014/0005633 A1 | 1/2014 | Finan |
| 2014/0018730 A1 | 1/2014 | Muller-Pathle |
| 2014/0032549 A1 | 1/2014 | McDaniel et al. |
| 2014/0066886 A1 | 3/2014 | Roy et al. |
| 2014/0074033 A1 | 3/2014 | Sonderegger et al. |
| 2014/0088428 A1 | 3/2014 | Yang et al. |
| 2014/0108046 A1 | 4/2014 | Cabrera et al. |
| 2014/0114277 A1 | 4/2014 | Eggert et al. |
| 2014/0121635 A1 | 5/2014 | Hayter |
| 2014/0128839 A1 | 5/2014 | Dilanni et al. |
| 2014/0129951 A1 | 5/2014 | Amin et al. |
| 2014/0135880 A1 | 5/2014 | Baumgartner et al. |
| 2014/0142508 A1 | 5/2014 | Dilanni et al. |
| 2014/0146202 A1 | 5/2014 | Boss et al. |
| 2014/0163664 A1 | 6/2014 | Goldsmith |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0038898 A1 | 2/2015 | Palmer et al. |
| 2015/0041498 A1 | 2/2015 | Kakiuchi et al. |
| 2015/0057913 A1 | 2/2015 | Benhammou |
| 2015/0119666 A1 | 4/2015 | Brister et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0165119 A1 | 6/2015 | Palerm et al. |
| 2015/0173674 A1 | 6/2015 | Hayes et al. |
| 2015/0193585 A1 | 7/2015 | Sunna |

(56) References Cited

U.S. PATENT DOCUMENTS

| | | |
|---|---|---|
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0290391 A1 | 10/2015 | Schmid et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0356250 A1 | 12/2015 | Polimeni |
| 2015/0366945 A1 | 12/2015 | Greene |
| 2016/0015891 A1 | 1/2016 | Papiorek |
| 2016/0019352 A1 | 1/2016 | Cohen et al. |
| 2016/0022905 A1 | 1/2016 | Nagar et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0184517 A1 | 6/2016 | Baek et al. |
| 2016/0220181 A1 | 8/2016 | Rigooard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0339172 A1 | 11/2016 | Michaud et al. |
| 2016/0354543 A1 | 12/2016 | Cinar et al. |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0216524 A1 | 8/2017 | Haider et al. |
| 2017/0239415 A1 | 8/2017 | Hwang et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0280609 A1 | 10/2018 | Nishimura et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De Wever et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0135319 A1* | 4/2020 | Vleugels ............... G16H 20/17 |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CA | 2863379 A1 | 8/2013 |
| CN | 1297140 A | 5/2001 |
| CN | 101208699 A | 6/2008 |
| CN | 201134101 Y | 10/2008 |
| DE | 4200595 A1 | 7/1993 |
| DE | 19756872 A1 | 7/1999 |
| EP | 0026056 A1 | 4/1981 |
| EP | 0341049 A2 | 11/1989 |
| EP | 0496305 A2 | 7/1992 |
| EP | 0549341 A1 | 6/1993 |
| EP | 0867196 A2 | 9/1998 |
| EP | 0939451 A1 | 9/1999 |
| EP | 1177802 A1 | 2/2002 |
| EP | 1376759 A2 | 1/2004 |
| EP | 1491144 A1 | 12/2004 |
| EP | 0801578 B1 | 7/2006 |
| EP | 1762263 A1 | 3/2007 |
| EP | 1839694 A1 | 10/2007 |
| EP | 1852703 A1 | 11/2007 |
| EP | 2099384 A1 | 9/2009 |
| EP | 2139382 A1 | 1/2010 |
| EP | 2353628 A2 | 8/2011 |
| EP | 2397181 A1 | 12/2011 |
| EP | 2468338 A1 | 6/2012 |
| EP | 2666520 A1 | 11/2013 |
| EP | 2695573 A2 | 2/2014 |
| EP | 2703024 A1 | 3/2014 |
| EP | 1874390 B1 | 10/2014 |
| EP | 2830499 A1 | 2/2015 |
| EP | 2943149 A1 | 11/2015 |
| EP | 3068290 A1 | 9/2016 |
| EP | 3177344 A1 | 6/2017 |
| EP | 3187201 A1 | 7/2017 |
| EP | 3193979 A1 | 7/2017 |
| EP | 3314548 A1 | 5/2018 |
| EP | 1571582 B1 | 4/2019 |
| EP | 2897071 B1 | 5/2019 |
| EP | 3598942 A1 | 1/2020 |
| EP | 3607985 A1 | 2/2020 |
| ES | 2559866 T3 | 2/2016 |
| FR | 2096275 A5 | 2/1972 |
| GB | 1125897 A | 9/1968 |
| GB | 1401588 A | 7/1975 |
| GB | 2176595 A | 12/1986 |
| GB | 2443260 A | 4/2008 |
| GB | 2443261 A | 4/2008 |
| GB | 2461086 A | 12/2009 |
| GB | 2495014 A | 3/2013 |
| GB | 2524717 A | 10/2015 |
| GB | 2525149 A | 10/2015 |
| JP | 51125993 A | 11/1976 |
| JP | 02131777 A | 5/1990 |
| JP | 2001190659 A | 7/2001 |
| JP | 2003154190 A | 5/2003 |
| JP | 2005326943 A1 | 11/2005 |
| JP | 2007144141 A1 | 6/2007 |
| JP | 2004283378 A | 10/2007 |
| JP | 2007307359 A | 11/2007 |
| JP | 2008513142 A1 | 5/2008 |
| JP | 2008242502 A | 10/2008 |
| JP | 2012210441 A | 11/2012 |

(56)    References Cited

FOREIGN PATENT DOCUMENTS

| | | | |
|---|---|---|---|
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 200048112 | A2 | 9/1968 |
| WO | 8606796 | A1 | 11/1986 |
| WO | 9800193 | A1 | 1/1998 |
| WO | 9801071 | A1 | 1/1998 |
| WO | 9819145 | A1 | 5/1998 |
| WO | 9824495 | A1 | 6/1998 |
| WO | 9841267 | A1 | 9/1998 |
| WO | 9855073 | A1 | 12/1998 |
| WO | 9910040 | A1 | 3/1999 |
| WO | 9910049 | A1 | 3/1999 |
| WO | 9956803 | A1 | 11/1999 |
| WO | 9962576 | A1 | 12/1999 |
| WO | 0010628 | A2 | 3/2000 |
| WO | 0013580 | A1 | 3/2000 |
| WO | 0019887 | A1 | 4/2000 |
| WO | 0030705 | A1 | 6/2000 |
| WO | 200032258 | A1 | 6/2000 |
| WO | 0061215 | A1 | 10/2000 |
| WO | 0078210 | A1 | 12/2000 |
| WO | 0172354 | A2 | 10/2001 |
| WO | 2001078812 | A1 | 10/2001 |
| WO | 2002015954 | A1 | 2/2002 |
| WO | 0226282 | A2 | 4/2002 |
| WO | 2002043866 | A2 | 6/2002 |
| WO | 2002076535 | A1 | 10/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2003097133 | A1 | 11/2003 |
| WO | 2004043250 | A1 | 5/2004 |
| WO | 2005110601 | A1 | 5/2004 |
| WO | 2004092715 | A1 | 10/2004 |
| WO | 2005031631 | A2 | 4/2005 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2006060668 | A2 | 6/2006 |
| WO | 2007064835 | A2 | 6/2007 |
| WO | 2007066152 | A2 | 6/2007 |
| WO | 2007078937 | A1 | 7/2007 |
| WO | 2007112034 | A2 | 10/2007 |
| WO | 2008024810 | A2 | 2/2008 |
| WO | 2008024814 | A2 | 2/2008 |
| WO | 2008029403 | A1 | 3/2008 |
| WO | 2008133702 | A1 | 11/2008 |
| WO | 2009023634 | A2 | 2/2009 |
| WO | 2009032399 | A1 | 3/2009 |
| WO | 2009039203 | A2 | 3/2009 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010022069 | A2 | 2/2010 |
| WO | 2010025433 | A1 | 3/2010 |
| WO | 2010053702 | A1 | 5/2010 |
| WO | 2010077279 | A1 | 7/2010 |
| WO | 2010078434 | A2 | 7/2010 |
| WO | 2010132077 | A1 | 11/2010 |
| WO | 2010138848 | A1 | 12/2010 |
| WO | 2010139793 | A1 | 12/2010 |
| WO | 2010146579 | A1 | 12/2010 |
| WO | 2010147659 | A2 | 12/2010 |
| WO | 2011012465 | A1 | 2/2011 |
| WO | 2011031458 | A1 | 3/2011 |
| WO | 2011075042 | A1 | 6/2011 |
| WO | 2011095483 | A1 | 8/2011 |
| WO | 2011133823 | A1 | 10/2011 |
| WO | 2012045667 | A2 | 4/2012 |
| WO | 2012073032 | A1 | 6/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013050535 | A2 | 4/2013 |
| WO | 2013078200 | A1 | 5/2013 |
| WO | 2013134486 | A2 | 9/2013 |
| WO | 2013149186 | A1 | 10/2013 |
| WO | 20130149186 | A1 | 10/2013 |
| WO | 2013177565 | A1 | 11/2013 |
| WO | 2013182321 | A1 | 12/2013 |
| WO | 2014029416 | A1 | 2/2014 |
| WO | 2014109898 | A1 | 7/2014 |
| WO | 2014110538 | A1 | 7/2014 |
| WO | 2014136105 | A1 | 9/2014 |
| WO | 2014149357 | A1 | 9/2014 |
| WO | 2014179774 | A1 | 11/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015117082 | A1 | 8/2015 |
| WO | 2015117854 | A1 | 8/2015 |
| WO | 2015167201 | A1 | 11/2015 |
| WO | 2015177082 | A1 | 11/2015 |
| WO | 2015187366 | A1 | 12/2015 |
| WO | 2015187793 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2016181384 | A2 | 11/2016 |
| WO | 2017004278 | A1 | 1/2017 |
| WO | 2017089289 | A1 | 6/2017 |
| WO | 2017091624 | A1 | 6/2017 |
| WO | 2017105600 | A1 | 6/2017 |
| WO | 2017184988 | A1 | 10/2017 |
| WO | 2017187177 | A1 | 11/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019043702 | A1 | 3/2019 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2020124058 | A1 | 6/2020 |
| WO | 2021011738 | A1 | 1/2021 |

OTHER PUBLICATIONS

International Search Report and Written Opinion for International Patent Application No. PCT/US2022/029012, mailed Aug. 19, 2022, 12 pages.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2021/047690, mailed Jan. 14, 2022, 13 pages.

International Search Report and Written Opinion for the International Patent Application No. PCT/US2022/055745, mailed Feb. 14, 2022, 13 pages.

International Search Report and Written Opinion for the International Patent Application No. PCT/US2021/053162, mailed Mar. 28, 2022, 18 pages.

(56) References Cited

OTHER PUBLICATIONS

International Search Report and Written Opinion for the International Patent Application No. PCT/US2021/064041, mailed Apr. 29, 2022, 11 pages.
International Search Report and Written Opinion for the International Patent Application No. PCT/US2022/015809, mailed Jun. 20, 2022, 15 pages.
European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
U.K. Intellectual Property Office, GB Application No. GB 1401587.9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.
U.K. Intellectual Property Office, GB Application No. GB 1401588.7, "Search Report under Section 17(5)" Aug. 17, 2015, 1 page.
U.K. Intellectual Property Office, GB Application No. GB 1401589.5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 pages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

(56)            References Cited

OTHER PUBLICATIONS

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Andrenko et al., "EM Analysis of PBG Substrate Microstrip Circuits for Integrated Transmitter Front End" MMET Proceedings, 295-297 (2000).

Bardi et al., "Plane Wave Scattering From Frequency-Selective Surfaces by the Finite-Element Method" IEEE Transactions on Magnetics 38(2):641-644 (2002).

Chappell et al., "Composite Metamaterial Systems for Two-Dimensional Periodic Structures" IEEE, 3840387 (2002).

Cheng et al., "Preparation and Characterization of (Ba, Sr) TiO3 thin films using interdigitial electrodes" Microelectronic Engineering, 66:872-879 (2003).

Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).

Diaz et al., "Magnetic Loading of Artificial Magnetic Conductors for Bandwidth Enhancement" IEEE, 431-434 (2003).

Hansen "Effect of a High-Impedance Screen on a Dipole Antenna" IEEE Antennas and Wireless Propagation Letter, 1:46-49 (2002).

Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).

Kern et al., "Active Negative Impedance Loaded EBG Structures for the Realization of Ultra-Wideband Artificial Magnetic Conductors" IEEE, 427-430 (2003).

Kern et al., "The Synthesis of Metamaterial Ferrities for RF Applications Using Electromagnetic Bandgap Structures" EEE, 497-500 (2003).

Kern et al., "Ultra-thin Electromagnetic Bandgap Absorbers Synthesized via Genetic Algorithms" IEEE, 1119-1122 (2003).

Kuhn et al., "Characterization of novel mono- and bifacially active semi-transparent crystalline silicon solar cells" IEEE Transactions on Electron Devices, 46(10): 2013-2017 (1999).

Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).

Lee et al., "Investigation of Electromagnetic Bandgap (EBG) Structures for Antenna Pattern Control" IEEE, 1115-1118 (2003).

Mckinzie III et al., "Mitigation of Multipath Through the Use of an Artificial Magnetic Conductor for Precision CPS Surveying Antennas" IEEE, 640-643.

Monorciho et al., "Synthesis of Artificial Magnetic Conductors by Using Multilatered Frequency Selective Surfaces" EEE Antennas and Wireless Propagation Letters, 1:196-1999 (2002).

Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).

Pontes et al., "Study of the dielectric and ferroelectric properties of chemically processed BaxSr1-xTiO3 thin films" Thin Solid Films, 386(2)91-98 (2001).

Rogers et al., "AMCs Comprised of Interdigital Capacitor FSS Layers Enable Lower Cost Applications" IEEE, 411-414 (2003).

Sievenpiper et al., "Two-Dimensional Beam Steering Using an Electrically Tunable Impedance Surface" IEEE Transactions on Antennas and Propagation, 51(10):2713-2722(2003).

Sun et al., "Efficiency of Various Photonic Bandgap (PBG) Structures" 3rd Int'l. Conf. on Microwave and Millimeter Wave Technology Proceedings, 1055-1058 (2002).

Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).

Vest "Metallo-organic decomposition (MOD) processing of ferroelectric and electro-optic films: A review" Ferroelectrics, 102(1):53-68 (1990).

Viviani et al., "Positive Temperature Coefficient of Electrical Resistivity below 150k of Barium Strontium Titanate" J. Amer. Ceram. Soc. 87(4): 756-758 (2004).

Weily et al., "Antennas Based on 2-D and 3-D Electromagnetic Bandgap Materials" IEEE, 847-850 (2003).

Yang et al., "Surface Waves of Printed Antennas on Planar Artificial Periodic Dielectric Structures" IEEE Transactions on Antennas and Propagation 49(3): 444-450 (2001).

Zhang et al., "Planar Artificial magnetic Conductors and Patch Antennas" IEEE Transactions on Antennas and Propagation, 51(10):2704-2712 (2003).

Ziroff et al., "A Novel Approach for LTCC Packaging Using a PBG Structure for Shielding and Package Mode Suppression" 33rd European Microwave Conference—Munich 419-422 (2003).

International Search Report and Written Opinion for Application No. PCT/US17/61336, mailed on Jan. 25, 2018, 9 pages.

"Graph Chart." iconfinder.com. Aug. 15, 2016. Accessed Apr. 21, 2020. Available online at URL: https://www.iconfinder.com/iconsets/graph-chart-2>.

"Circular Progress Indicator Component for React." reactscript.com. Dec. 2, 2016. Accessed Sep. 9, 2020. Available online at URL: <http://reactscripts.com/circular-progress-indicator-component-react/>.

Kruska, Michal. "Circle progress bar." dribbble.com. Oct. 18, 2012. Accessed Apr. 21, 2020. Available online at URL: <https://dribbble.com/shots/775718-Circle-progress-bar>.

"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-xamarin-forms>.

International Search Report and Written Opinion for Application No. PCT/US2021/047685 mailed on Dec. 6, 2021, 15 pages.

Team Section—Qonto, by Christophe Kerebel, dated Dec. 12, 2018, dribbble.com [online]. Retrieved Jul. 1, 2022 from Internet <URL:https://dribbble.com/shots/5676730-Team-Section-Qonto> (Year: 2018).

"Circular Loader." dribbble.com. Nov. 19, 2015. Accessed Jul. 24, 2019. Available online at URL: https://dribbble.com/shots/2362441-Circular-Loader (Year: 2015).

"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- -knobs-range-slider> (Year: 2015).

"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).

"Tick and cross circle shape icon . . ." depositphotos.com. Aug. 27, 2016. Accessed Feb. 1, 2019. Available online at URL:<https://depositphotos.com/121291612/stock-illustration-tick-and-cross-circle-shape.html> (Year: 2016).

"Vector-Vector Illustration of Preloader / Buffer Shapes, or Dials with Knobs." 123rf.com. Date not available. Accessed Oct. 25, 2018. Available online at URL: <https://www.123rf.com/photo_37292689_stock-vector-vector-illustration- -of-preloader-buffer-shapes-or-dials-with-knobs.html> (Year: N/A).

Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).

Obaizamomwan, Osas. "How to use the new features in iOS 9 Notes App." iphonehacks.com. Sep. 12, 2015. Accessed Apr. 24, 2018.

(56) References Cited

OTHER PUBLICATIONS

Available online at URL: https://www.iphonehacks.com/2015/09/how-to-use-the-new-features-in-ios-9-notes-app.html.

International Search Report and Written Opinion for the International Patent Application No. PCT/US21/064056, mailed Apr. 4, 2022, 12 pages.

International Search Report and Written Opinion for the International Patent Application No. PCT/US21/064170, mailed Apr. 20, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (2008, July).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on IOS 11", GoToTags, Sep. 11, 2017, web <https://gototags.com/blog/read-nfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 bages.

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010 (OPTIS. 247VPC).

International Search Report and Written Opinion in PCT/US2008/079641 (Optis.203VPC) dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

(56) References Cited

OTHER PUBLICATIONS

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

* cited by examiner

400b

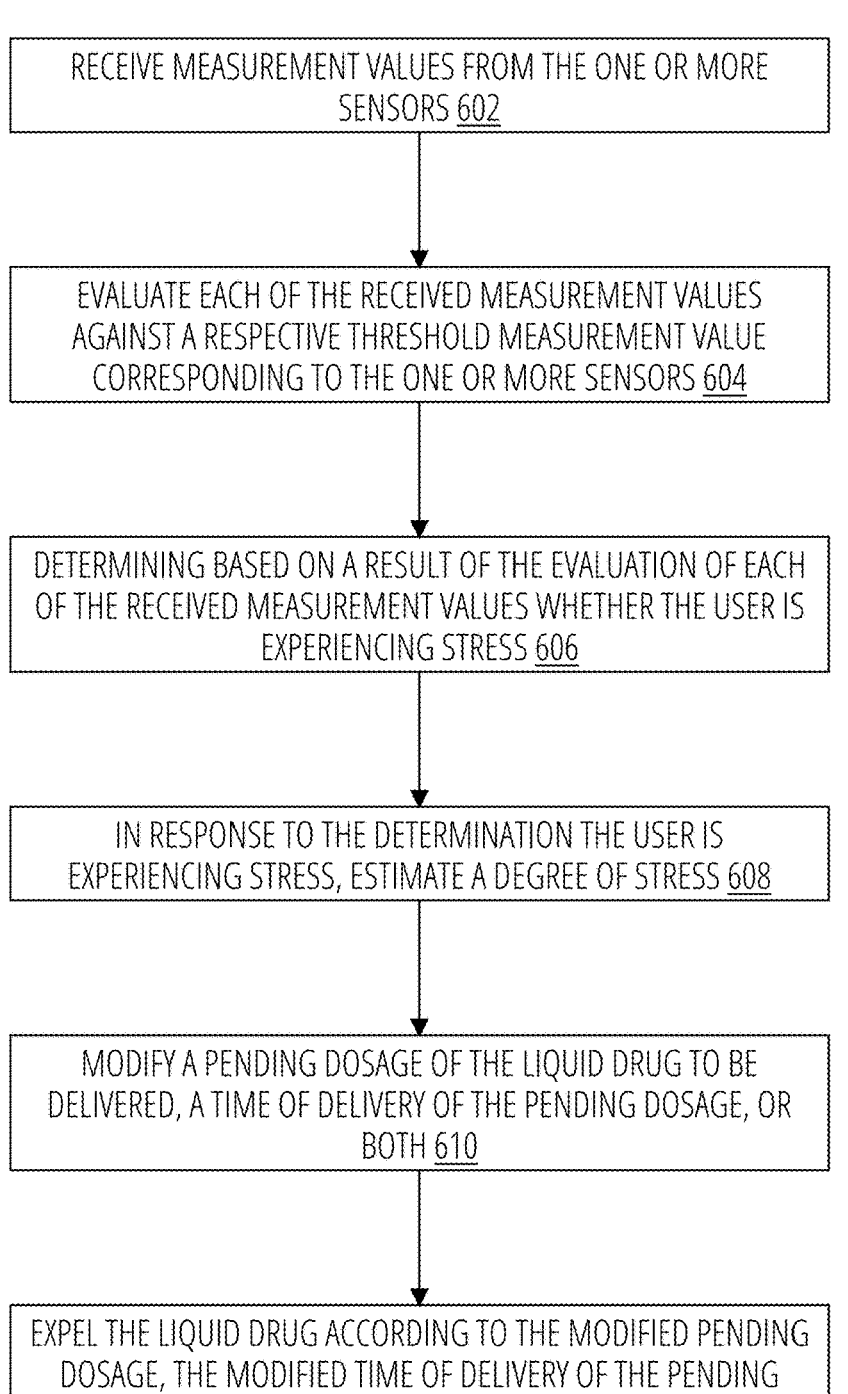

RECEIVE MEASUREMENT VALUES FROM THE ONE OR MORE SENSORS 602

EVALUATE EACH OF THE RECEIVED MEASUREMENT VALUES AGAINST A RESPECTIVE THRESHOLD MEASUREMENT VALUE CORRESPONDING TO THE ONE OR MORE SENSORS 604

DETERMINING BASED ON A RESULT OF THE EVALUATION OF EACH OF THE RECEIVED MEASUREMENT VALUES WHETHER THE USER IS EXPERIENCING STRESS 606

IN RESPONSE TO THE DETERMINATION THE USER IS EXPERIENCING STRESS, ESTIMATE A DEGREE OF STRESS 608

MODIFY A PENDING DOSAGE OF THE LIQUID DRUG TO BE DELIVERED, A TIME OF DELIVERY OF THE PENDING DOSAGE, OR BOTH 610

EXPEL THE LIQUID DRUG ACCORDING TO THE MODIFIED PENDING DOSAGE, THE MODIFIED TIME OF DELIVERY OF THE PENDING DOSAGE, OR BOTH 612

FIG. 6

ADAPTATION OF MEDICAMENT DELIVERY IN RESPONSE TO USER STRESS LOAD

RELATED APPLICATIONS

This application claims the benefit of U.S. Provisional Patent Application No. 63/227,275, filed Jul. 29, 2021, the contents of which are incorporated herein by reference in their entirety.

BACKGROUND

Patients with Type I diabetes often encounter unexplained excursions in their blood glucose readings. They are frustrated that the insulin delivery that worked perfectly on one day does not seem to work well on another day. There are several factors that can influence sensitivity to insulin, its counterparts, or combinations of insulin and other medicaments, such factors including time of day, exercise patterns, stress, and the like. Day to day living has many stress-inducing situations, for example taking tests and exams for students, business meetings for adults, driving in dense traffic, visits to a doctor or a dentist, a multitude of emotional situations, and similar situations.

It is well known that stress may affect blood glucose levels in Type I diabetes patients. For example, stress can induce activation of adrenergic hormones and cortisol, which can increase glucose production and increase insulin resistance as well. Stress can further change a user's habits, such as eating more or less, forgoing exercise, and the like. Experimental studies suggest that stress affects people in different ways. It has been observed to have negligible effect on some, increase in blood glucose levels in some and decrease in blood glucose levels in others for similar stressors.

The timing of the stress also has bearing on the glycemic outcome. For instance, studies of stressful events in and around mealtime have noted that the carbohydrate consumption was reduced on days with higher stress levels, and as a result, the user's blood glucose level may differ from meal-times that do not coincide with the stressful events. Studies have reported hypoglycemic excursions to be more likely. The hypoglycemia excursions are likely either because of over-treating stress elevated blood glucose levels with insulin or a reduction in carbohydrate consumption or both. Furthermore, increased stress levels have been found to be correlated with elevated blood glucose variability and glycemic instability.

It would be beneficial if a system or process was provided that was operable to counter the effects of stress by modifying drug delivery to avoid the hypoglycemia excursions caused by over-treating stress elevated blood glucose levels.

BRIEF SUMMARY

In one aspect, a drug delivery system including a drug delivery device and a sensor module is disclosed. The drug delivery device may include a processor, a memory, a drug container, and a pump drive mechanism. The sensor module may include one or more sensors. Each of the one or more sensors may be operable to measure a physiological condition of a user. The processor is communicatively coupled to the one or more sensors. The drug container may store a liquid drug. The pump drive mechanism may be coupled to the processor and to the drug container. The memory may be coupled to the processor and may include programming code. The processor, when executing the programming code, may be operable to receive measurement values from the one or more sensors, and evaluate each of the received measurement values against a respective threshold measurement value corresponding to the physiological condition measured by a respective sensor of the one or more sensors. The processor, based on a result of the evaluation of each of the received measurement values, may determine whether the user is experiencing stress. In response to the determination the user is experiencing stress, the processor may estimate a degree of stress, and modify a pending dosage of the liquid drug to be delivered, a time of delivery of the pending dosage, or both. The processor may expel the liquid drug according to the modified pending dosage, the modified time of delivery of the pending dosage, or both.

In another aspect, a method includes obtaining a respective measurement value from one or more sensors coupled to a body of a user, where each sensor of the one or more sensors obtains data related to a physiological condition of the user. Each obtained respective measurement value may be evaluated against a respective threshold measurement value corresponding to the one or more sensors, determining based on a result of the evaluation of each of the obtained respective measurement values whether the user is experiencing stress, in response to the determination the user is experiencing stress, estimating a degree of stress, modifying an imminent dosage of the liquid drug to be delivered, a time of delivery of the imminent dosage, or both, and expelling the liquid drug according to the modified imminent dosage, the modified time of delivery of the imminent dosage, or both.

In a further aspect, a non-transitory computer-readable storage medium is provided that includes instructions executable by a processor. Execution of the instructions causes the processor to obtain a respective measurement value from one or more sensors. Each sensor of the one or more sensors may obtain data related to a physiological condition of a user. Each obtained respective measurement value is evaluated against a respective threshold measurement value corresponding to the one or more sensors. The processor determines, based on a result of the evaluation of each of the obtained respective measurement values, a degree of stress the user is experiencing. In response to the determination of the degree of stress the user is experiencing, the processor may modify an imminent dosage of a liquid drug to be delivered, a time of delivery of the imminent dosage, or both; and cause the liquid drug to be expelled according to the modified imminent dosage, the modified time of delivery of the imminent dosage, or both.

BRIEF DESCRIPTION OF THE DRAWINGS

FIG. 6 illustrates a flowchart of an example of a process for modifying a liquid drug dosage based on a level of stress experienced by a user of a drug delivery system.

DETAILED DESCRIPTION

Figures 1A, 1B:
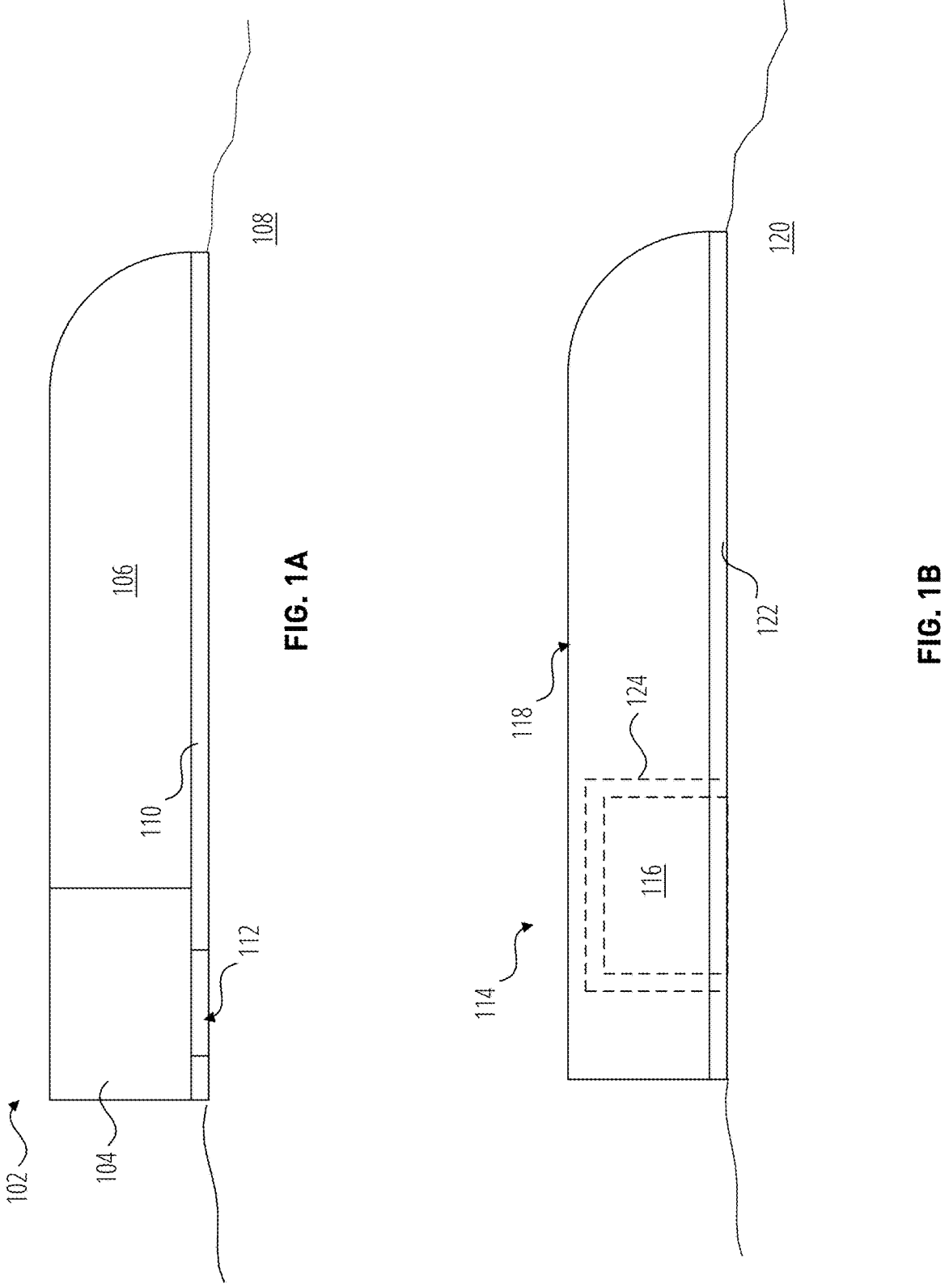
FIG. 1A illustrates an example of a drug delivery device on the skin of a user.
FIG. 1B illustrates another example of a drug delivery device on the skin of a user.

The drug delivery system disclosed herein is described with reference to the examples illustrated in the drawings. The drug delivery system may be an element or a component within a larger automatic medication delivery system. In the examples, the drug delivery system may include a drug delivery device and a sensor module as well as other components that are described throughout the specification. In different aspects, the drug delivery system is a wearable drug delivery system that is coupled to the body of a user and worn by the user over the course of several days.

FIG. 1A illustrates an example of a drug delivery system on the skin of a user. The example drug delivery system 102 includes a sensor module 104 and a drug delivery device 106. In the example of FIG. 1A, the sensor module 104 may snap fit to the drug delivery device 106. Once snap fitted, the sensor module 104 may be at least substantially flush with the bottom of the drug delivery system 102. The drug delivery system 102 may be coupled to skin 108 of a user via an adhesive layer 110. This example of sensor module 104 includes sensor skin access 112 via an opening in the adhesive layer 110. The sensor module 104 may include one or more sensors (shown in later examples). The sensor skin access 112 provides access to the skin of the user for the one or more sensors. For example, if a sensor of the one or more sensors is a skin conductance sensor, the sensor skin access 112 provides the sensor module 104 with access to the skin so a measurement of the skin conductance of the user may be obtained.

FIG. 1B illustrates another example of a drug delivery system on the skin of a user. The Drug delivery system 114 includes a sensor module 116 and a drug delivery device 118. The sensor module 116 may couple to the drug delivery device 118 via a module opening 124. The sensor module 116 may fit within the module opening 124 of the drug delivery device 118. Once fitted into the module opening 124, the sensor module 116 may be flush with the skin 120 of a user. The drug delivery system 114 is held in place on the skin 120 by an adhesive layer 122 on a bottom surface of the drug delivery device 118.

The sensor module 116 may include one or more sensors that detect physiological conditions of a user. Examples of the different types of sensors that may be utilized as the one or more sensors are described below.

Figure 2:
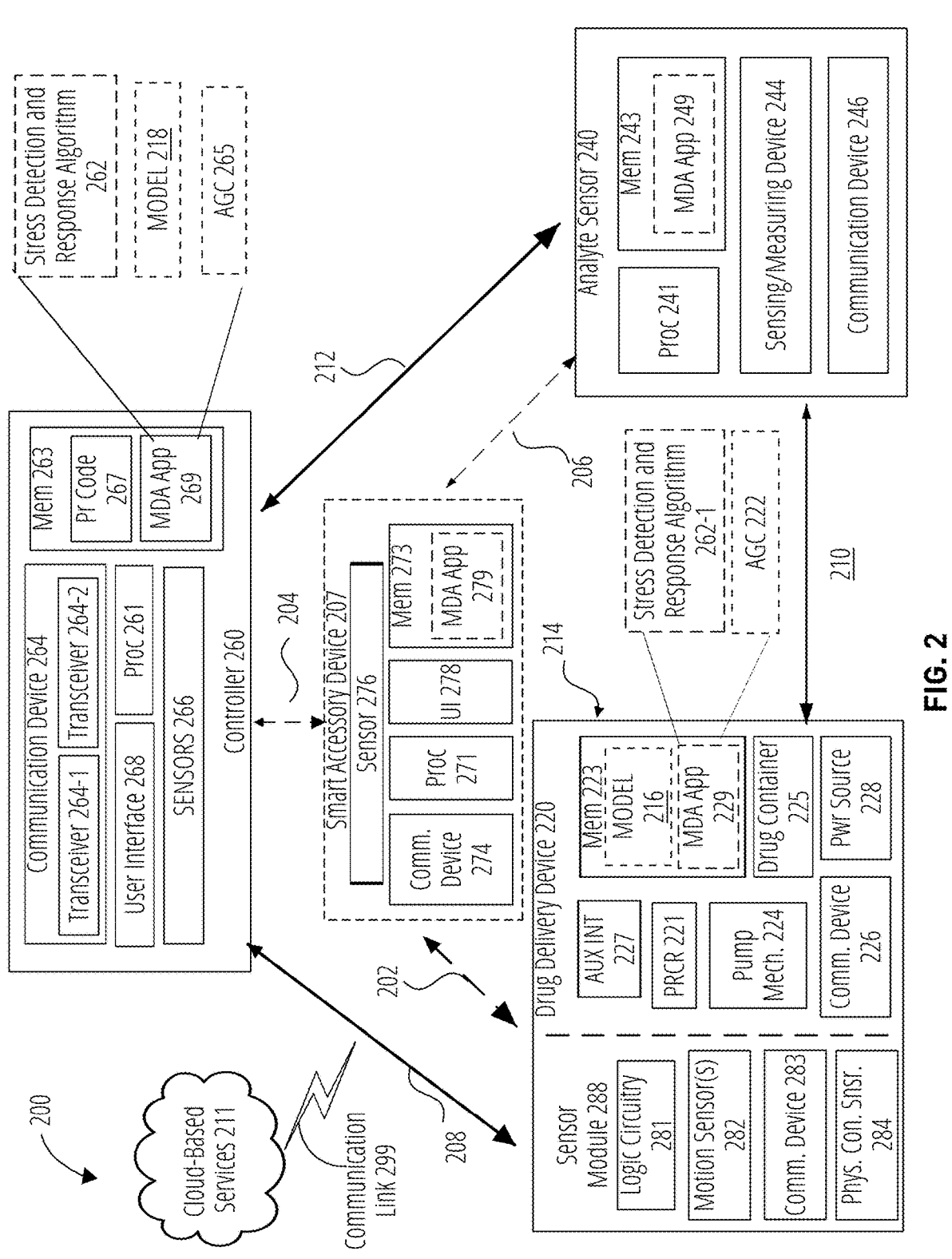
FIG. 2 illustrates an example of an automatic medication delivery system incorporating an example of the drug delivery system in accordance with another aspect of the disclosed subject matter.

FIG. 2 illustrates a functional block diagram of a system example suitable for implementing the example processes and techniques described herein.

The drug delivery system environment 200 includes components that collectively may form an automatic drug delivery system that is operable to deliver a liquid drug without any user interaction, or, in some examples, with limited user interaction, such as in response to depressing a button to indicate confirmation of a recommended dosage of the liquid drug, or the like.

The drug delivery system environment 200, in some examples, may include a controller 260, a drug delivery system 214, an analyte sensor 240, and cloud-based services 211. In another example, the drug delivery system environment 200 may include a controller 260, a drug delivery system 214, an analyte sensor 240, cloud-based services 211 as well as the smart accessory device 207. In yet another example, the drug delivery system environment 200 may include a drug delivery system 214, and an analyte sensor 240. In any of the examples of the drug delivery system environment 200, the cloud-based services 211 as well as the smart accessory device 207 may be optional.

Different systems or devices of the drug delivery system environment 200 may implement (and/or provide functionality for) a medication delivery algorithm or application (MDA). An example of an MDA may be an artificial pancreas (AP) application or an automatic glucose control algorithm or application, each of which may be operable to govern or control automated delivery of a drug or medication, such as insulin, to a user (e.g., to maintain euglycemia—a normal level of glucose in the blood). The MDA may, for example, receive information from additional applications or algorithms that execute on a device within the drug delivery system environment 200, such as a stress detection and response algorithm or application 262. Instances of the stress detection and response algorithm or application 262, such as stress detection and response algorithm or application 262-1, may be executed on processors of other respective devices or systems within the drug delivery system environment 200, such as the drug delivery device 220, the analyte sensor 240 or, when present, the smart accessory device 207.

The drug delivery system 214 may include a drug delivery device 220 and a sensor module 288. The drug delivery device 220 may be operable to perform and execute the processes described in the examples of FIGS. 1A-2 without input from the controller 260 or the optional smart accessory device 207. The drug delivery device 220, in the example drug delivery system 214, may include an auxiliary interface 227, a processor (PRCR) 221, a pump mechanism 224, a communication device 226, a memory 223, a power source 228, and a drug container 225.

The sensor module 288 may include logic circuitry 281, a motion sensor(s) 282, a communication device 283, and a physiological condition sensor 284 (labeled as Phys. Con. snsr. in the figure). The logic circuitry 281 may be operable to receive raw data from the respective motion sensor(s) 282 and physiological condition sensor 284, process the received raw data, and output measurement values corresponding to the physiological condition and/or motion data. The motion sensor(s) 282 may be one sensor or a number of different sensors, such as an accelerometer and a gyroscope that are operable to detect orientation and movement of a user that may be associated with participation in physical activity. The physiological condition sensor 284 may include one or more sensors such as those shown in later examples. The physiological condition sensor 284 may be operable to detect physiological attribute data of a user, such as a heart rate of the user, a blood oxygen saturation level of the user, an analyte level or concentration (e.g., blood glucose or hormone) of the user, or a combination of physiological attributes using the listed sensors or different sensors. Measurement values corresponding to the detected physiological attributes may be determined from the detected physiological attribute data either by the sensor itself (e.g., the output from the sensor may be a measurement value) or logic circuitry 281 or the processor 221 of the drug delivery device 220. Both the motion sensor 282 and the physiological condition sensor 284 may be operable to output a signal (or multiple signals) containing the detected physiological attribute data.

The processor 261 of the controller 260 may be operable to receive signals generated by the sensor module 288 from the drug delivery device 220 and may be further operable to make the determination of whether the user participated in exercise, a type of the exercise and a category of the exercise, such as aerobic or anaerobic. In a further alternative, the partial processing of the sensor data (e.g., accelerometer data or gyroscope data) may occur at the logic circuitry 281, the processor 221 and the processor 261 of the controller 260. In addition, or alternatively, the processor 271 of the smart accessory device 207 may perform some of the processing of the sensor data or may facilitate transfer of the sensor data from the drug delivery device 220 to the controller 260.

In an operational example, the physiological condition sensor 284 may include an accelerometer, a gyroscope and/or a heart rate monitor. The processor 221 may be further operable to evaluate the different data provided by the respective sensors within the sensor module 288 to further classify the activity of the user as physical activity. Based on the determinations from the different data provided by the sensors 282 and 284, the stress detection and response algorithm may cause the presentation of different prompts or statistics based on the determinations on a user interface 268 of the controller 260.

The processor 221 alone may implement the processes to determine a response to the detection of stress as described with respect to the other examples, based on inputs from the sensor module 288. The processor 221 of the drug delivery device 220 may be operable to control delivery of a drug to the user according to a drug treatment plan, diabetes treatment plan, or other drug delivery regimen stored in the memory 223. For example, the processor 221 may be operable to execute programming code and be configured when executing non-transitory programming code of a medication delivery application or algorithm, such as MDA APP 229 and other programs, such as a stress detection and response algorithm 262 and an Automatic Glucose Control (AGC) 265, to perform the functions that implement the example routines and processes described herein. In an operational example, the processor 221, when executing the programming code implementing MDA APP 229, may be operable to output a control signal causing actuation of the pump mechanism 224 to deliver drug dosages or the like as described with reference to the examples of FIGS. 1A, 1B and 3-11.

The memory 223 may store programming code executable by the processor 221. The programming code, for example, may enable the processor 221 to control expelling insulin from the container 225 and control the administering of doses of medication based on execution of the MDA APP 229, AGC 265, stress detection and response algorithm or application 262, or, based on signals from external devices. For example, the drug delivery device 220 may be operable to receive and respond to the external control signals and be operable to deliver a drug based on information received from the analyte sensor 240, the cloud-based services 211 and/or the controller 260 or optional smart accessory device 207. The memory 223 may also be operable to store other data and programming code, such as the stress detection and response algorithm 262-1. The memory 223 may also store models, such as model 218, which may be an individualized stress load model or another type of machine learning model.

The container 225 may be operable to store different categories of drugs (or medications or therapeutic agents), such as chemotherapy drugs, pain relief drugs (e.g., morphine), diabetes treatment drugs (e.g., insulin, glucagon, pramlintide, glucagon-like peptides, or combinations thereof), blood pressure medication, or the like.

In an example, the drug delivery device 220 includes a communication device 226, which may be a receiver, a transmitter, or a transceiver that operates according to one or more radio-frequency protocols, such as Bluetooth, Wi-Fi, a near-field communication standard, a cellular standard, or the like. The processor 221 in addition communicating with the sensor module 288 may, for example, communicate with the controller 260 and an analyte sensor 240 via the communication device 283.

When operable to communicate with an external device, such as the controller 260 or the analyte sensor 240, the drug delivery device 220 may receive signals over the communication link 208 from the controller 260 or communication link 210 from the analyte sensor 240. The processor 221 of the drug delivery device 220 may receive and process the signals from the respective external devices (e.g., cloud-based services 211, smart accessory device 207, or controller 260) to determine whether the user is experiencing stress and, respond by implementing (or modifying) delivery of a drug to mitigate the effects of the experienced stress and may be operable to deliver the different categories of drugs (or medications), such as those mentioned above.

The logic circuitry 281 of the sensor module 288 may be integrated circuits (ICs), application specific ICs (ASICs), field programmable arrays (FPGAs), and/or programmable logic devices (PLDs), or the like, that are operable to receive signals from the respective motion sensors 282, communication device 283 and physiological condition sensor 284. In an example, if the received signals need processing, the logic circuitry 281 may be operable to process the received signals and output a processed signal. Alternatively, if processing is unnecessary, the logic circuitry 281 may be operable to forward the received signals for output. When the sensor module 288 is coupled to the drug delivery device 220, the logic circuitry 281 may be communicatively coupled either via wired couplings (e.g., electrical contacts) to the auxiliary interface 227 or a wireless link, such as Bluetooth, to the communication device 226 that may be communicatively coupled to the auxiliary interface 227 of the drug delivery device 220.

In the drug delivery device 220, the auxiliary interface 227 is coupled to the processor 221 and provides signals received from the sensor module 288 to the processor 221. The processor 221 is operable to process the sensor module 288 signals received via the auxiliary interface 227. When the processor 221 executes the programming code stored in the memory 223, such the MDA APP 229 and the stress detection and response algorithm 262-1, the processor 221 may be operable to determine whether a user of the drug delivery device 220 is experiencing stress.

The processor 221 may determine whether the user is experiencing stress based on the model 216 that may be stored in the memory 223. The model 216 may be an individualized stress load model as described with reference to later examples.

With regard to the motion sensors 282, a determination of whether a user is participating in physical activity is relevant to the processor since some physiological responses to physical activity, such as elevated heart rate, increased skin conductance and the like, are similar to physiological responses to stress. By comparing measurement values derived from the motion sensor data, the processor 221 may be operable to determine that the user is participating in physical activity instead of experiencing mental stress, and vice versa.

The processor 221 when executing the MDA APP 229 may output a control signal operable to actuate the pump mechanism 224 to deliver a drug, such as insulin, in response to a determination of a user experiencing stress. Both the determination of a user experiencing stress and the response are described with reference to later examples.

The drug delivery device 220 may be a component of a wearable automatic drug delivery system that may be attached to the body of a user, such as a patient or diabetic, at an attachment location via an adhesive layer (as shown in other figures) and may deliver any therapeutic agent, any drug or medicine, such as insulin or the like, to a user at or around the attachment location.

The drug delivery device 220 may, for example, include a container 225 for storing the drug (such as insulin), a needle or cannula (not shown in this example) for delivering the drug into the body of the user (which may be done subcutaneously, intraperitoneally, or intravenously), and a pump mechanism 224 for transferring the drug from the container 225 through a needle or cannula and into the user. The pump mechanism 224 may be fluidly coupled to container 225, and communicatively coupled to the processor 221.

The smart accessory device 207, may be a device such as a smartwatch, a personal assistant device, a fitness device, or the like, which may communicate with the other components of drug delivery system environment 200 via either a wired or wireless communication links 206, 108 or 110. The smart accessory device 207 may be, for example, an Apple Watch®, other wearable smart device, including eyeglasses, provided by other manufacturers, a global positioning system-enabled wearable, a wearable fitness device, smart clothing, or the like.

The smart accessory device 207 may include a communication device 274, a processor 271, a user interface 278, a sensor 276, and a memory 273. The user interface 278 may be a graphical user interface presented on a touchscreen display of the smart accessory device 207. The sensor 276 may include a heart rate sensor, a blood oxygen saturation sensor, a skin conductance sensor, an accelerometer, a gyroscope, a combination of these sensors, or the like. The output from the sensor 276 or sensors of sensor 276 may be used by the stress detection and response algorithm or application 262 or stress detection and response algorithm or application 262-1. The memory 273 may store programming code to operate different functions of the smart accessory device 207 as well as an instance of the MDA APP 279. The processor 271 may execute programming code, such as the MDA APP 279 for controlling the wearable automatic drug delivery device 220 to implement the examples described herein.

The controller 260 may be a computing device such as a smartphone, a tablet, a personal diabetes controller, a dedicated diabetes therapy controller, personal diabetes management (PDM) device, or the like. In an example, the controller 260 may include a processor 261, a controller memory 263, a user interface 268, and a communication device 264. The controller 260 may contain analog and/or digital circuitry that may be implemented as a processor 261 for executing processes based on programming code stored in the controller memory 263, such as the MDA algorithm or application (APP) 269, to manage a response to a user participating in exercise. The controller 260 may be used to initially set up, adjust settings, and/or control operation of the wearable automatic drug delivery device 220 and/or the analyte sensor 240 as well as the optional smart accessory device 207.

The processor 261 may also be operable to execute programming code stored in the controller memory 263, such as programming code 267 and the MDA APP 269. The MDA APP 269 may include additional applications, models and processes, such as stress detection and response algorithm or application 262, model 218 and automatic glucose control application 265.

The user interface 268 may be controlled by the processor 261 and be operable to present a graphical user interface that enables the input of a confirmation of a stress level, input of a stress level, a number of carbohydrates, an indication of physical activity, adjustment of setting selections, and the like.

The communication device 264 may include one or more transceivers such as transceiver 264-1 and transceiver 264-2 and receivers or transmitters that operate according to one or more radio-frequency protocols. In the example, the transceivers 264-1 and 264-2 may be a cellular transceiver and a Bluetooth® transceiver, respectively. For example, the transceivers 264-1 and 264-2 may be operable to receive and transmit signals containing information usable by the MDA APP 269, the AGC 265 and the stress detection and response algorithm or application 262.

In some examples, the controller 260 may include a user interface 268, respectively, such as a keypad, a touchscreen display, levers, light-emitting diodes, buttons on a housing (shown in another example) of the controller 260, a microphone, a camera, a speaker, a display, or the like, that is operable to allow a user to enter information and allow the controller 260 to output information for presentation to the user (e.g., alarm signals or the like). The user interface 268 may provide inputs, such as a voice input, a gesture (e.g., hand or facial) input to a camera, swipes to a touchscreen, or the like, to processor 261 which the programming code 267 and/or MDA App 268 interprets.

The analyte sensor 240 may include a processor 241, a memory 243, a sensing/measuring device 244 and a communication device 246. The analyte sensor 240 may be communicatively coupled to the processor 261 of the controller 260 or processor 221 of the wearable automatic drug delivery device 220. The memory 243 of the analyte sensor 240 may be operable to store information and programming code, such as an instance of the MDA APP 249.

The analyte sensor 240 may be operable to detect multiple different analytes, such as lactate, ketones, uric acid, sodium, potassium, alcohol levels, hormone levels, or the like, and output results of the detections, such as measurement values or the like. The analyte sensor 240 may, in an example, be operable to measure a blood glucose value at a predetermined time interval, such as every 5 minutes, or the like. The communication device 246 of analyte sensor 240 may have circuitry that operates as a transceiver for communicating the measured blood glucose values to the controller 260 over a wireless link 212 or with wearable automatic drug delivery device 220 over the wireless communication link 208. While called an analyte sensor 240, the sensing/measuring device 244 of the analyte sensor 240 may include one or more additional sensing elements, such as a glucose measurement element, a hormone detection element, a heart rate monitor, a pressure sensor, or the like. The processor 241 may include discrete, specialized logic and/or components, an application-specific integrated circuit, a microcontroller or processor that executes software instructions, firmware, programming instructions stored in memory (such as memory 243), or any combination thereof.

Like the processor 221, the processor 241 of the analyte sensor 240 may be operable to perform many functions. For example, the processor 241 may be configured by the programming code stored in the memory 243 to manage the collection and analysis of data detected the sensing and measuring device 244 and deliver the results of the analysis and/or the data to the controller 260, the drug delivery device 220, or both.

Although the analyte sensor 240 is depicted in FIG. 2 as separate from the wearable automatic drug delivery device 220, in various examples, the analyte sensor 240 and wearable automatic drug delivery device 220 may be incorporated into the same unit. That is, in various examples, the analyte sensor 240 may be a part of the wearable automatic drug delivery device 220 and contained within the same housing of the wearable automatic drug delivery device 220 (e.g., the sensor 240 or, only the sensing/measuring device 244 and memory storing related programming code may be positioned within or integrated into, or into one or more components, such as the memory 243, of, the wearable automatic drug delivery device 220).

The communication link 299 that couples the cloud-based services 211 to the respective devices 220, 240, 260 or 207 in the drug delivery system environment 200 may be a cellular link, a Wi-Fi link, a Bluetooth link, or a combination thereof. Services provided by cloud-based services 211 may include data storage that stores anonymized data, such as blood glucose measurement values, drug delivery history, bolus delivery history, time data, stress level histories, a blood glucose measurements in response to stress, individualized stress load models, and other forms of data. Using various authentication protocols and other security precautions, the cloud-based services 211 may provide user-specific data for use by the MDA App 269 and stress detection and response algorithm or application 262.

The wireless communication links 202, 204, 206, 208, 210, 212 and 299 may be any type of wireless link operating using known wireless communication standards or proprietary standards. As an example, the wireless communication links communication links 202, 204, 206, 208, 210, 212 and 299 may provide communication links based on Bluetooth®, Zigbee®, Wi-Fi, a near-field communication standard, a cellular standard, or any other wireless protocol via the respective communication devices 264-1, 264-2, 226, 246 and 274.

Software related implementations of the techniques described herein, such as the processes examples described with reference to FIGS. 1A-11 may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Stress is typically quantified subjectively on a scale. Different scales of stress are used, but a common scale is the Likert scale, which rates the stress level on a scale from 0-10. In the Likert scale, a rating value 0 (zero) represents No Stress at All, a rating level of 5 represents "Moderate Stress" and a rating level of 10 represents an "Extremely Stressful" situation. The Likert scale stress level ratings are sometimes used in subjective surveys of a user's stress during different situations. For example, a survey may ask in a first question what is a person's stress level when sitting in a meeting of peers, and in a second question may ask what is the person's stress level when they are presenting subject matter in a meeting of peers. Physiological conditions, such as heart rate, blood glucose level, skin temperature, skin conductance, blood pressure, blood oxygen levels and the like, of the person are likely to change between when the person is sitting in a meeting and when the person is presenting subject matter in the meeting. Using measurements of physiological conditions, a system may be able to establish an estimate of the stress level a user is experiencing based on the physiological condition measurements.

When a user has an elevated stress level, the user's blood glucose level increases, which is one of the body's way of adapting to the stress. While a blood glucose level is necessarily elevated during times of stress and due to the body's natural response, diabetics are unable to accommodate the increased glucose. As a result, the user's blood glucose measurement values tend to continue to increase even in response to countermeasures taken by the user or by an automatic glucose control system. A normal functioning pancreas would respond during times of stress by increasing insulin output. However, the pancreas of a Type 1 diabetic (T1DM) patient is unable to do this, and a Type 2 diabetic (T2DM) patient has limited capability to cope with the elevated blood glucose levels because insulin sensitivity is impacted during periods of stress.

When setting up the stress detection and response algorithm or application on a user device, an initial set-up phase may include the system observing patterns in variation of the outputs of sensors that detect a user's physiological condition, such as heart rate, skin temperature and skin conductance. Baseline patterns through the day and over the course of several days may be learned and used as an estimate of the degree of stress the user is experiencing. For example, night-time patterns may be one baseline, hourly rest periods may provide other baselines, a user's normal working hours yet another baseline, a child's bath time or bedtime may provide another stress event, and so on. In addition, a user may be prompted to input a stress level, such as a Likert scale value, a customized scale as used herein, or the like. In a further example, a machine learning framework may be implemented to recognize, and model stress based on the inputs from the one or more sensors of a sensor module or sensor from an external device, such as the smart accessory device 207 or the like.

Figure 3:
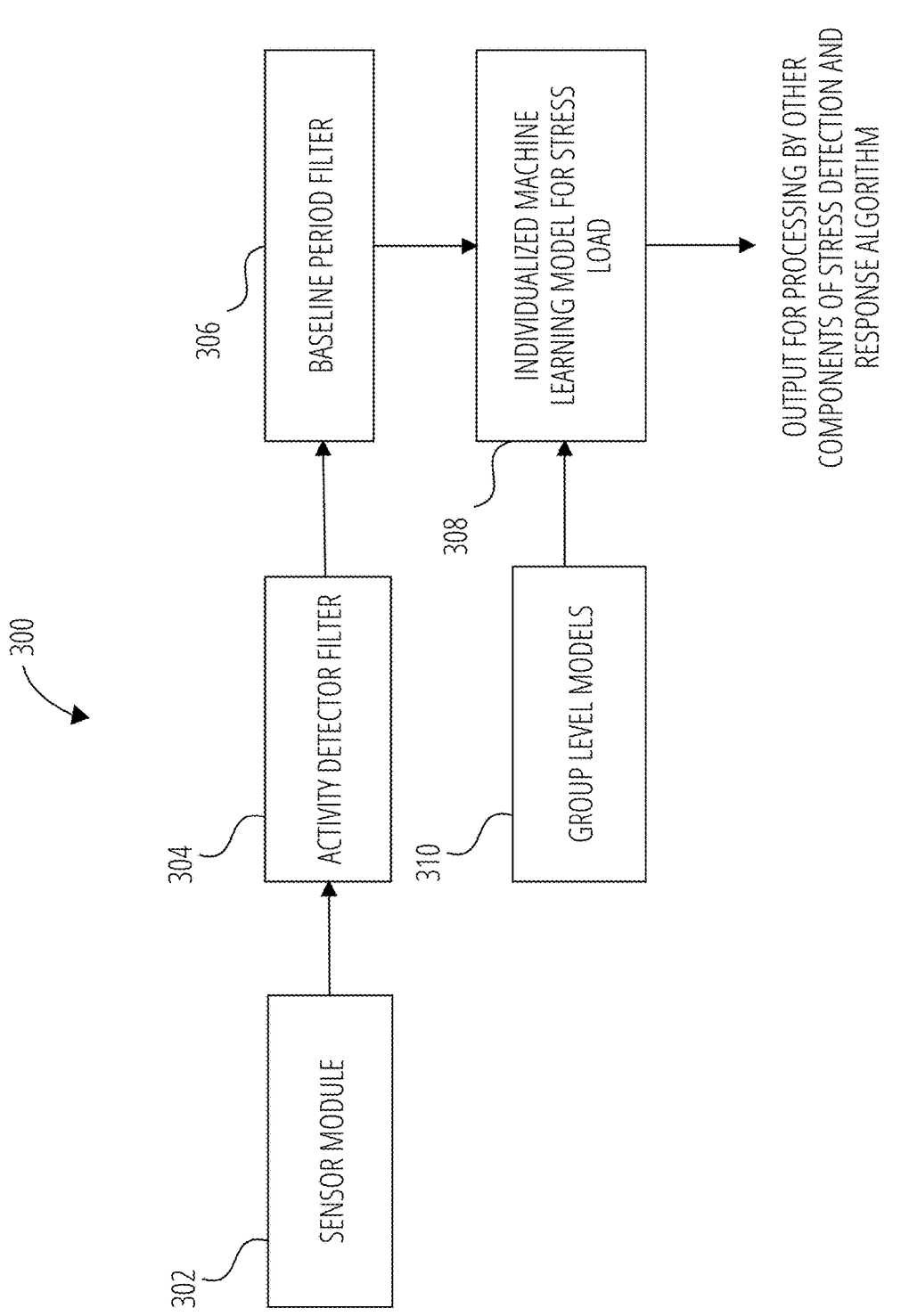
FIG. 3 shows a functional block diagram of an aspect of the disclosed subject matter.

FIG. 3 shows a functional block diagram of configuring a machine learning model according to an aspect of the disclosed subject matter. The process 300 illustrates the various functions for training a machine learning model for responding to stress. The process 300 may be executed by a processor, which may be executing a stress detection and response algorithm, such as 221 of drug delivery device 220 or 261 of controller 260 as shown in FIG. 2. The sensor module 302 may provide input signals to a stress detection and response algorithm executing on the processor. The stress detection and response algorithm may be configured to train the individualized machine learning model for stress load 308 according to the process 300.

The stress detection and response algorithm may receive inputs from sensor module 302 and provide updates to several components. For example, the stress detection and response algorithm may include an activity detector filter 304, a baseline period filter 306, an individualized machine learning model for stress load 308, and group level models 310. The individualized machine learning model for stress load 308 may be used by the stress detection and response algorithm to provide an input to an automatic glucose control application based on an evaluation of data provided by the sensor module 302 and the stress level experienced by the user.

The sensor module 302 may include a heart rate monitor, a skin conductance detector, a skin temperature detector, and the like. The sensor module 302 may also include an accelerometer and clock for a time of day. Alternatively, the stress detection and response algorithm may obtain accelerometer and clock information from a processor executing the stress detection and response algorithm or from an external device, such as a smart accessory device, fitness device or the like.

With regard to a heart rate monitor, a person's heart rate is known to change with the person's stress level. The stress detection and response algorithm may be operable to extract features in the time domain and the frequency domain from signals input from the heart rate sensor and serve as input to the individualized machine learning model for stress load 308.

Postural heart rate measurement is more robust. As an example, a user's minimum heart rate (HR) while sitting may be 67+/−10 beats per minute, while standing be 79+/−10 beats per minute, and while stressed be 102+/−12 beats per minute. In response to situations identified as stressful, heart rate variability measured by power spectral analysis has been known to show an increase in low frequency (LF) power (a marker of sympathetic activity) and a concomitant decrease in high frequency (HF) power (a measurement of vagal activity). Respective power determinations may be made using Fourier analysis of the input signals obtained from the heart rate sensor and/or other sensors. Experimental observation has revealed values of (78±11%, 22±11%, LF %, HF %), as compared to a minimum HR value of (61±16%, 39±16%, LF %, HF %), or Standing (68±11%, 32±11%, LF %, HF %). Using measurements of a user's heart rate variability as inputs, the stress detection and response algorithm may continue to train the individualized machine learning model for stress load 308 to provide an output indicative of a response to the stress experienced by the user. The learning process 300 may be specific to the heart rate variability measurements and may be combined with later learning related to other measurements, such as blood glucose measurement values, skin conductance measurements, or the like.

The sensor module 302 may include other sensors, such as a skin conductance sensor. Skin conductance values have been shown to change as a result of stress. For example, stress activates sweat glands, and the skin conductance level is noted to increase as a result. Using the latency of response and peak of response relative to baseline levels of skin conductance may be used estimate a degree of stress the user is experiencing. Since skin conductance changes in response to increased perspiration from sweat glands, the stress detection and response algorithm may be operable to determine whether the user is participating in physical activity or coping with high humidity or high temperature environmental conditions or currently experiencing stress. The stress detection and response algorithm may, for example, be operable to obtain location information and weather-related information based on the location to obtain environmental conditions the user's may be experiencing, in addition to obtaining information that may be indicative of user exercise, such as heart rate information and accelerometer data.

In addition, skin temperature has been noted to be reduced during stress. Sampling the skin temperature at a high frequency and determining each of a minimum skin temperature, the maximum skin temperature, mean skin temperature and/or a standard deviation of these measurements has been shown to recognize stress levels of a user. The stress detection and response algorithm may be operable to determine whether the user's environment is at a reduced temperature, e.g., at high altitude, during wintertime, or the like. The processor may be operable to recognize stress levels of the user based on the determined minimum skin temperature, the determined maximum skin temperature, and the determined standard deviation.

In another sensor example, the stress detection and response algorithm may obtain an accelerometer signal from the sensor module 302.

When building the individualized machine learning model for stress load 308, the process may utilize an activity detector filter 304 to filter out periods of activity and enable relatively quiescent periods to be used in the model. The time of day can also be effectively used to capture, for example, baseline nighttime readings. The signal inputs may be received by the activity detector filter 304 of the stress detection and response algorithm. The activity detector filter 304, for example, may use an accelerometer signal as a marker of physical activity. An elevated heart rate, changes to skin conductance and changes of skin temperature are also expected when physical activity is performed. In some examples, the activity detector filter 304 may be accelerometer-based and use the accelerometer signal to determine the user is participating in physical activity and may exclude these periods from consideration by the stress detection and response algorithm. In some examples, the activity detector filter 304 may, in addition to making accelerometer-based decisions, also make determinations based on heart rate, skin conductance or skin temperature. Prior to the sensor information being processed by either the baseline period filter 306 or individualized machine learning model for stress load 308, the activity detector filter 304 may limit the data provided by eliminating periods of time during which the user is participating in physical activity. The output of the activity detector filter 304 may be a signal indicative of the physical activity state.

With the periods when the user is participating in physical activity filtered out, the stress detection and response algorithm may further filter the inputs received from the sensor module 302. The baseline period filter 306 may further filter the sensor data received from the sensor module 302 based on a time of day (for example, night-time, before a meal, after a meal, and the like) that may be filtered out as typically time periods during which the user's stress is not elevated beyond a threshold, such as a 3 or 4 rating. The output from the baseline period filter 306 may be used as a baseline for the user. For example, the heart rate (e.g., 65 beats per minute or the like) provided by a heart rate sensor of the sensor module 302 may be set as a baseline heart rate for the user, a skin conductance value (e.g., in the range of −0.2 V DC to +−0.2 V DC or −100 mV DC to +100 mV DC) provided by a skin conductance sensor of the sensor module 302 may be set as a baseline skin conductance value for the user and the same may be set for the skin temperature value output by the skin temperature sensor.

The stress detection and response algorithm may be operable to access different models that are tailored to different groups based on one or more of gender, age, stage of diabetes, weight, level of physical activity, occupation or the like. The different models may be accessible from the group level models 310, which may be stored in a memory. Using the group level models 310, the stress detection and response algorithm may tailor the individualized machine learning model for stress load 308 to the user based on the output of the baseline period filter 306.

In an example, the individualized machine learning model for stress load 308 may be a model component that is built using an initial model from group level models 310 and the outputs of baseline period filter 306. A model component may be hardware, software or firmware that is used to implement a modeling circuit or modeling algorithm. For example, a group level model from the group level models 310 may be selected based on user information, such as type of diabetes, insulin sensitivity, physical activity level, age, gender, or the like. The selected model from the group level models 310 may receive baseline settings for heart rate variability, such as a baseline heart rate, baseline heart rate low frequency power level, baseline heart rate high frequency power level, as well as a baseline skin conductance value, and the like from the baseline period filter 306. After a period of time, which may be 24 hours, 48 hours or the like, for training, an individualized machine learning model for stress load 308 may be formulated. For example, the training for the individualized machine learning model for stress load 308 may produce a rule set, which may be established using a machine learning algorithm by the stress detection and response algorithm. The rule set may be used as the individualized machine learning model for stress load 308.

In an example, the stress level may be modeled on a scale of 0 to 4 like a typical Likert-type scale based on the individual level maximal variations of heart rate, heart rate variability, and skin conductance are compared to the user's respective baseline values. The population level variations in the sensor values provided by the sensor module 302 may be additionally used to develop a model of the stress scale. The rule set of the individualized machine learning model for stress load 308 may consider various factors, such as heart rate, heart rate variability, and skin conductance.

In another example, the measured heart rate variability may be compared to a heart rate variability threshold (e.g., 20% variability or the like), and, in response to the measured heart rate variability exceeding the heart rate variability threshold, an indication that the user is experiencing stress may be generated. In a specific example, if the heart rate is elevated by more than 20% compared to the baseline heart rate, heart rate variability, indicated by the ratio of heart rate low frequency power level to heart rate high frequency power level (LF/HF), is greater than (>) 3.25, and the skin conductance (i.e., galvanic skin response) is elevated by 20% compared to baseline skin conductance, the stress level may be determined to be 3 out of the scale of 4.

After the initial set up of the stress detection and response algorithm, the individualized machine learning model for stress load 308 may make a determination of the stress level or stress load and output an indication of the user's stress level or stress load that may be processed by the stress detection and response algorithm. In response to the indication of the user's stress received from the individualized machine learning model for stress load 308, the stress detection and response algorithm may output an indication of the stress level, the stress level value or another notification or alert that the user is experiencing stress to an automatic glucose control algorithm or application, such as AGC 265 or AGC 222. The automatic glucose control algorithm or application may be operable to determine whether a user's drug treatment plan needs to be modified based on the indication of the stress level, the stress level value or another stress-related notification or alert. Examples of the modifications to be made to the drug treatment plan are described in later examples.

Figure 4A:
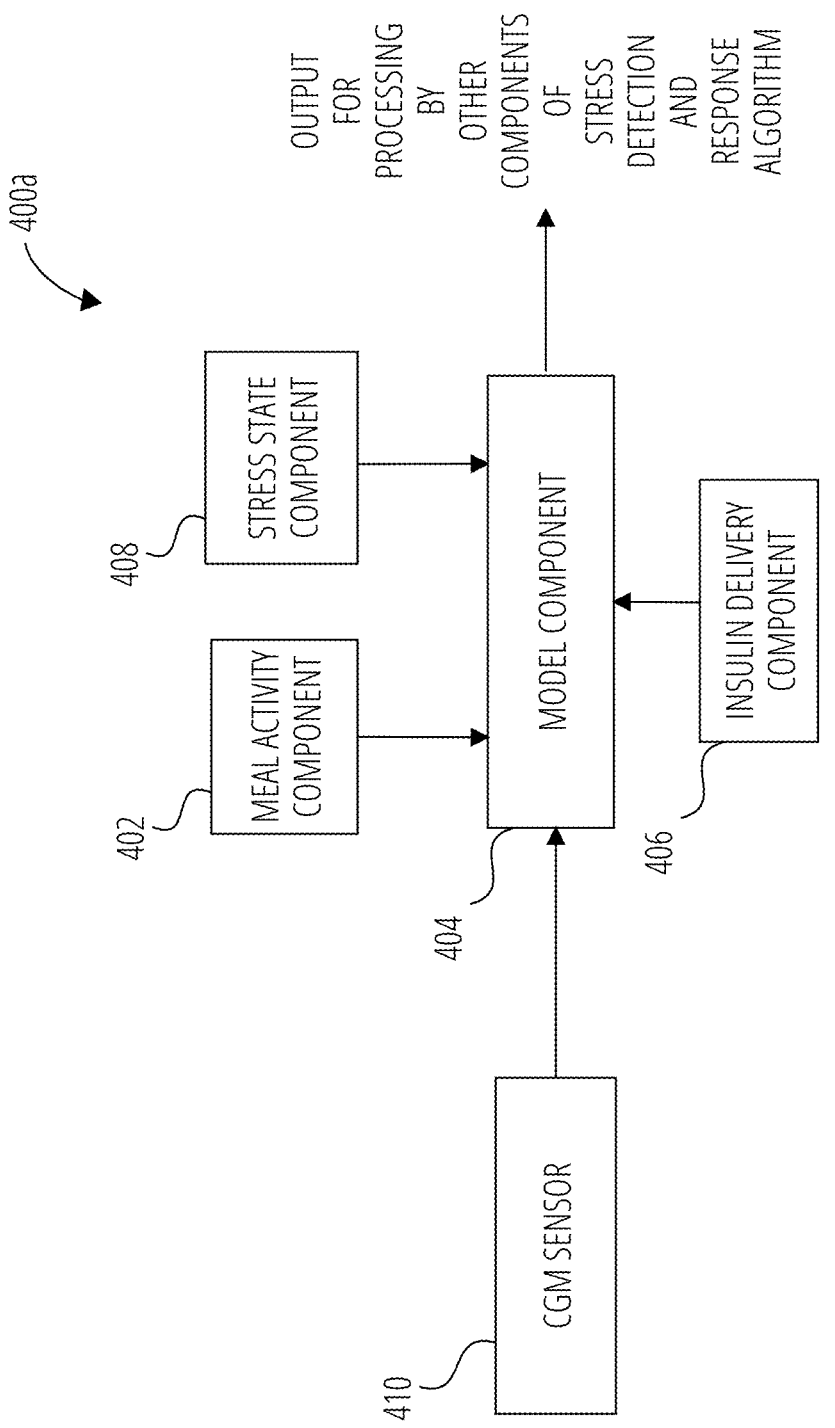
FIG. 4A shows another functional block diagram of an aspect of the disclosed subject matter.

FIG. 4A shows yet another block diagram of an aspect of the disclosed subject matter with respect to elevation of blood glucose levels due to stress.

In the process 400*a*, a CGM sensor 410 may provide input signals to a stress detection and response algorithm executing on a processor, such as processor 221 or processor 261 of FIG. 2. The stress detection and response algorithm may receive inputs from and provide updates to several components. For example, the stress detection and response algorithm may include a model component 404, a stress state component 408, a meal activity component 402, and an insulin delivery component 406. The model component 404 may provide an input to other components of a stress detection and response algorithm based on an evaluation of data provided by the CGM sensor 410 and the user's stress level. The stress state component 408 may be hardware circuits, software executed on a processor as part of a stress detection and response algorithm or a combination that is operable to receive inputs from sensors, such as the physiological condition sensor 284 in FIG. 2, or the sensors of sensor modules 302 of FIG. 3, and the like.

The meal activity component 402 may be hardware, software or firmware that responds to inputs related to meal consumption. The inputs may be from the CGM sensor 410, a user interface, such as 268 of FIG. 2, or the like. The model component 404 may be a machine learning circuit or software executed by a processor as part of a stress detection and response algorithm. A representative machine learning model usable as the model component 404 is a recurrent neural network, which is a type of deep neural network well suited for time series modeling with long and short term memory.

The model component 404 may be trained to model a user's blood glucose measurement values as the blood glucose measurement values rise above a baseline value, such as 120 mg/dL, for example, for the specific user.

Figure 4B:
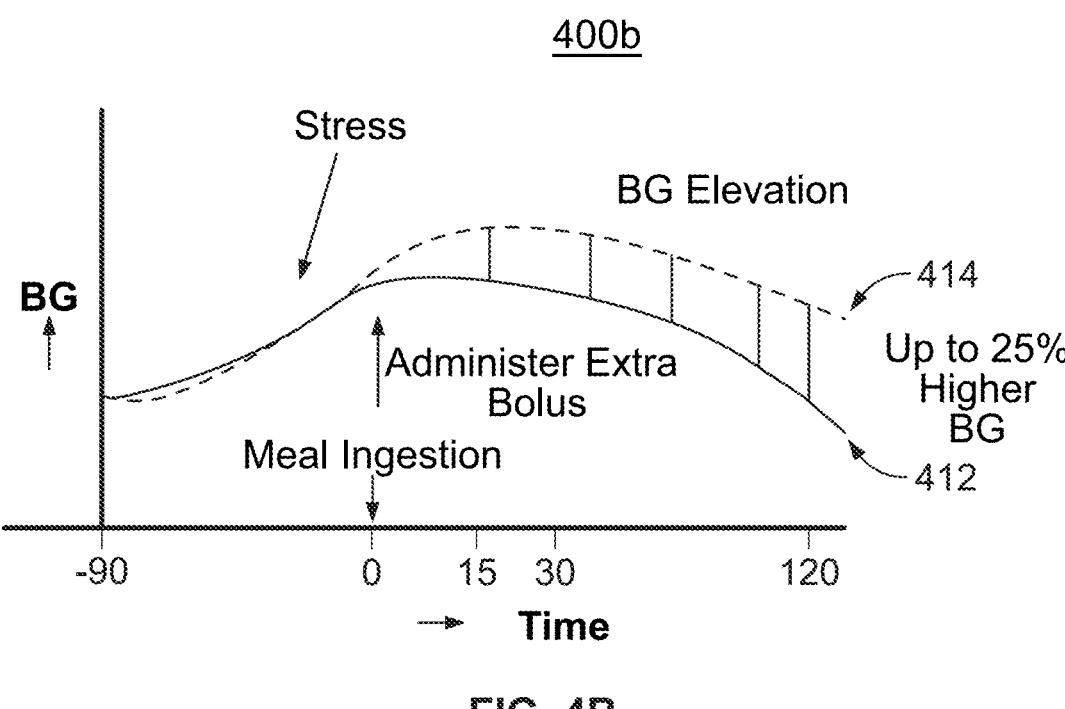
FIG. 4B is a graph illustrating the effects of stress on values of post prandial blood glucose levels.
Figure 4C:
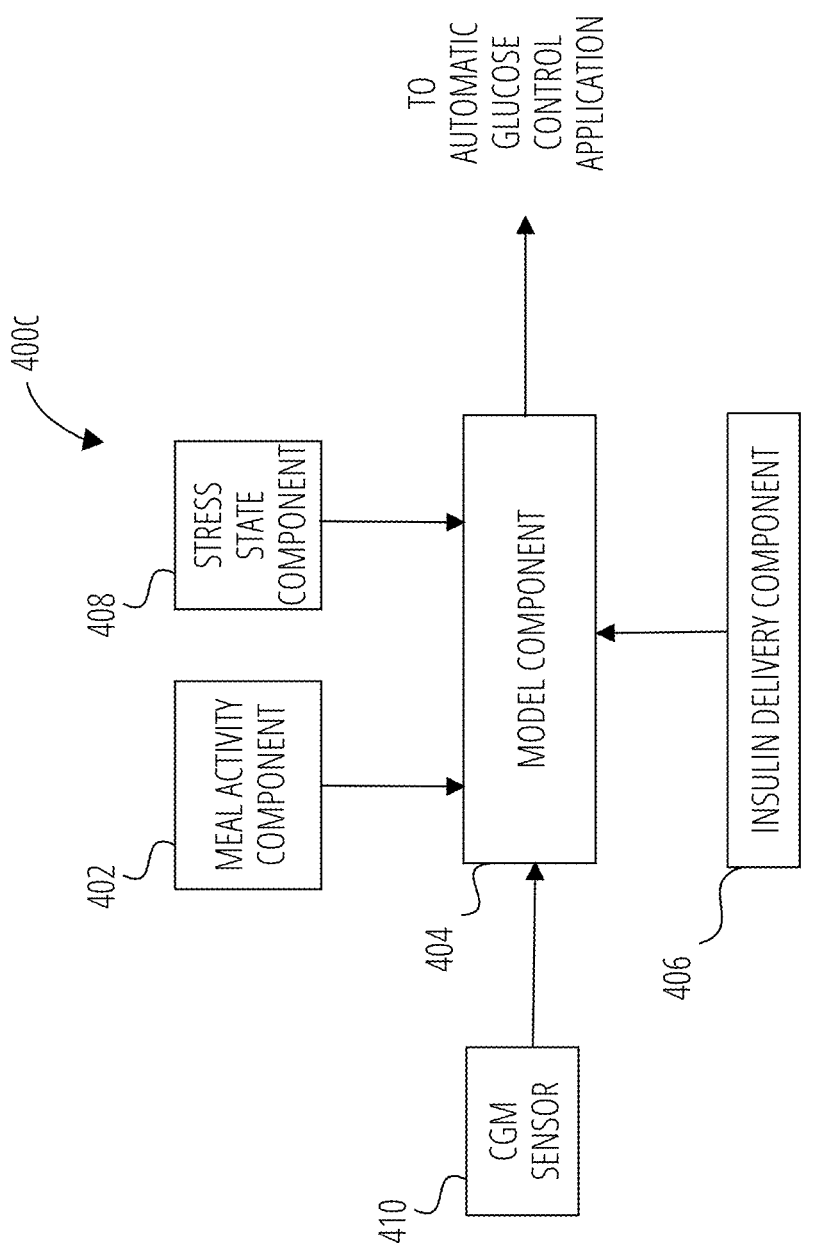
FIG. 4C shows yet another functional block diagram of an aspect of the disclosed subject matter.
Figure 4D:
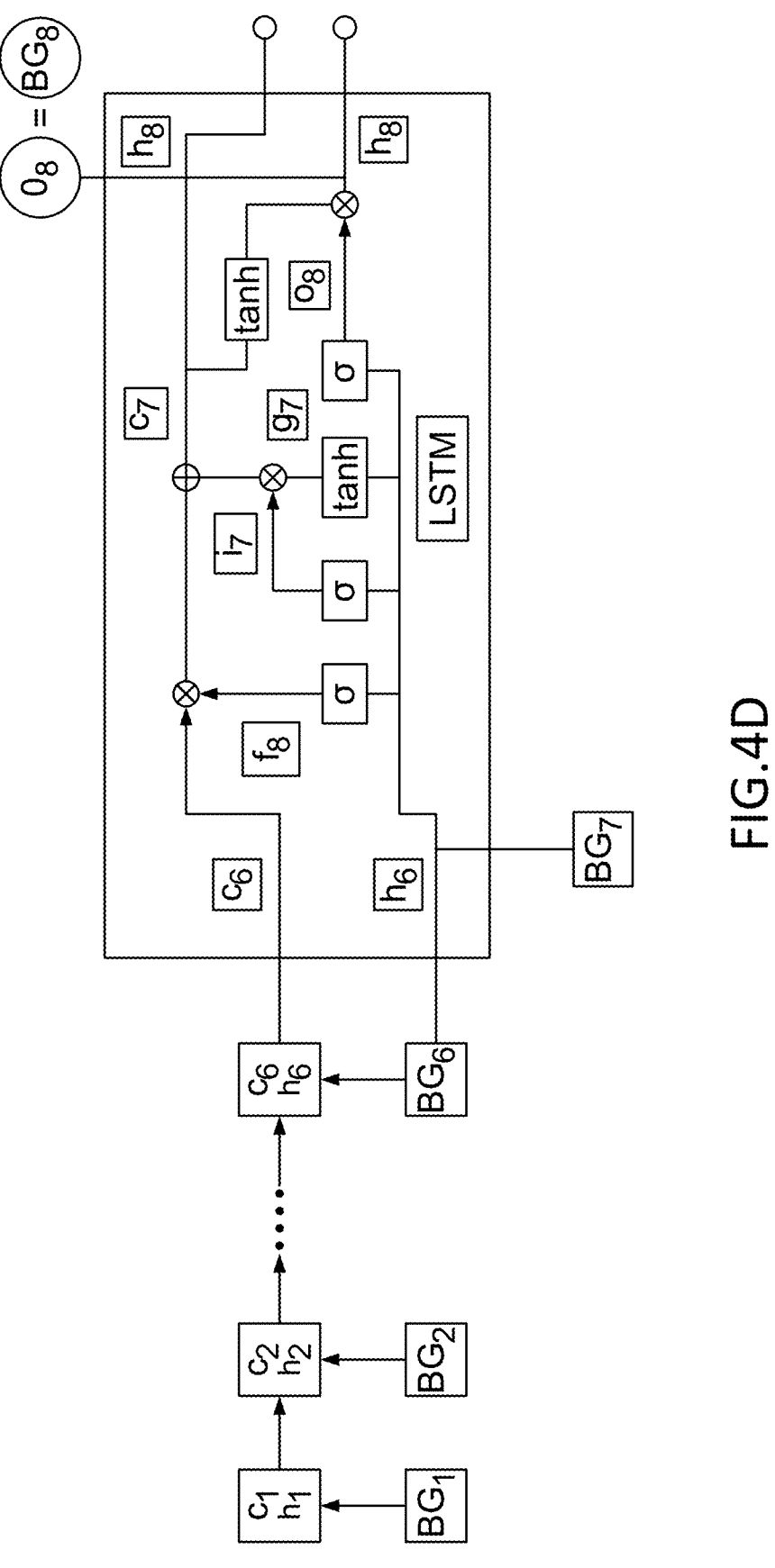
FIG. 4D illustrates an example of a recurrent neural network (RNN) in the form of a long short-term memory (LSTM) to estimate or predict future blood glucose measurement values based on past blood glucose measurement values.

FIG. 4D illustrates an example of a recurrent neural network (RNN) in the form of a long short-term memory being trained to estimate or predict future blood glucose measurement values based on past blood glucose measurement values. As an example of blood glucose prediction, we may have a sequence of values that span 30 minutes of data (7 data points spread at 5 minutes). The RNN can be used to predict the blood glucose measurement value after 30 minutes. For example, given a sequence of blood glucose measurement values BG1 through BG7, the RNN may be trained to predict a later blood glucose measurement value, such as BG8. In the example of FIG. 4D, the blood glucose measurement values: BG1, BG2, BG3, BG4, BG5, BG6, BG7 may cause the RNN to output BG8. The BG8 value may be used in subsequent training. For example, a typical training sequence may resemble:

BG1, BG2, BG3, BG4, BG5, BG6, BG7→output BG8;
BG2, BG3, BG4, BG5, BG6, BG7, BG8→output BG9;
BG3, BG4, BG5, BG6, BG7, BG8, BG9→output BG10; . . .
BG18, BG19, BG20, BG21, BG22, BG23, BG24→output BG25.

FIG. 4D shows the example LSTM type of recurrent neural network being trained with a sequence of 7 blood glucose measurement values ($BG_1$ to $BG_7$) to predict the $8^{th}$ value ($BG_8$). The above training framework may be extended with an input of greater than 7 blood glucose measurement values and an output greater than one blood glucose measurement value, for example, 2-10 estimated blood glucose measurement values may be output from the RNN. Also, the sequence of predictions may include additional input variables other than blood glucose measurement values. For example, the additional input variables may include inputs such as a stress value, an insulin dose and carbohydrate values to predict the sequence of blood glucose measurement values. The LSTM implementation is effective to mitigate and even eliminate the vanishing gradient problem that may occur when gradient-based learning methods and backpropagation is utilized.

In an operational example, the CGM sensor 410 may output information, such as blood glucose measurement values (such as 120 mg/dL), raw measurement data, or the like, to a processor executing the stress detection and response algorithm to be processed. For example, the processor may be operable to process the raw measurement data to a blood glucose measurement value. The blood glucose measurement value output from the CGM sensor 410 may be provided to the model component 404 for evaluation. In addition, the stress state component 404 may provide an indication of the stress state of the user that is filtered by meal activity component 402, which, in this example, indicated that there is no activity (i.e., no evidence of a meal or snack having been ingested). The output from the meal activity component 402 may be provided to the model component 404. As such, the meal activity component 402 may pass the stress level from the stress state component 408 unchanged or unmodified due to no activity.

In addition, the amount of insulin (i.e., insulin doses) that has been delivered to the user over a period of time is also input to the model component 404. In addition to the amount of insulin delivered, the time that the respective amounts were delivered may also be evaluated by the model component 404. For example, the effects of insulin diminish over time and it would be useful for the model component 404 to have an indication of whether the insulin doses were delivered within 30 minutes, 45 minutes, 60 minutes, or 90 minutes of the evaluation by the model component 404.

The input to the model component 404 may include a stress level (e.g., 0-4 or the like) filtered by the meal activity component 402 (which, in this case, is no activity), a sequence of blood glucose values prior to the stress, and a sequence of blood glucose values after the stress (noted by the increased blood glucose measurement values) from the CGM sensor 410, and the amounts of insulin that has been delivered to the user based on inputs from the insulin delivery component 406. Based on the inputs, the model component 404 may generate an output indicating an amount that the blood glucose may be elevated above baseline based on the presence of stress and with no meal activity. For example, the output from the model component 404 based on a respective stress state and an indication of the no meal the blood glucose measurement value may be as follows: if the stress level is 3, the blood glucose level may be elevated by 20 mg/dL above baseline for stress level 3; or if the stress level is 4, the blood glucose level may be elevated by 30 mg/dL above baseline for stress level 4. The specific increases in the blood glucose may be dependent on the specific individual's response to stress but after a period of training, the machine learning classifier of the model component 404 learns the specific individual's response to stress.

FIG. 4B is a graph illustrating the effects of stress on values of post prandial blood glucose levels that may be used in the training of model component 404.

As shown in graph 400b, a user's blood glucose measurement values may follow a trend shown by the lower line 412 under non-stressful or low-scale stress (i.e., the stress level on the stress scale being substantially equal to 0 or less than 1). Alternatively, in the presence of stress, for example, an event that causes stress (greater than 0 on the stress scale) may occur anytime between 90 minutes before ingestion of the meal (i.e., at time 0 (zero) in the graph 400b). In response to the stress being greater than 0, the user's blood glucose measurement values follow the upper line 414. Some research has shown that a user's post prandial blood glucose level remains elevated at levels up to 25% higher (i.e., the upper line 414) than a baseline meal (i.e., the lower line 412) when stress occurs during meal ingestion as shown in FIG. 4. In addition, studies have shown that when stress occurs after ingestion of a meal, there is a marked delay in the clearance of glucose by the body in both Type I diabetic patients and Type II diabetic patients. The glucose level has been noted to remain higher for 2 hours, at a level of approximately 25% higher than on non-stress days after a meal. Using this information, the process 400c may be implemented to model the effect of stress and ingestion of a meal on a user's blood glucose measurement values.

FIG. 4C shows another block diagram of an aspect of the disclosed subject matter with respect to elevation of blood glucose levels due to stress. FIG. 4C depicts the framework for learning by a model component the blood glucose pattern after ingestion of a meal. For example, the post prandial meal blood glucose rise may be modeled using the framework shown in FIG. 4C using a recurrent neural network or the like. The example of FIG. 4C differs from that of FIG. 4A in that the meal activity component 402 has detected that a meal has been ingested, and that the meal has a number X (in grams) of carbohydrates. The model component 404 may receive a blood glucose indication from the CGM sensor 410. The blood glucose indication may indicate a rise in the blood glucose of the user.

In the example of a post prandial evaluation of stress level, the inputs to the model component 404 may include: the number of grams of carbohydrates ingested during the meal from the meal activity component 402, a sequence of blood glucose measurement values prior to ingestion of the meal, a sequence of blood glucose measurement values after the meal both from the CGM sensor 410, or the like. The stress state component 408 may be operable to provide the stress level (using, for example, the 0-4 stress scale discussed above with reference to FIG. 3) and the approximate time of occurrence of the stress with respect to the time of ingestion of the meal.

In addition, the insulin delivery component 406 may provide an amount of insulin (with a time stamp) provided prior to ingestion of the meal, an amount of any insulin bolus provided in response to the meal (with a respective time stamp) and the like within a set period of time, such as 2-3 hours.

In the example, the model component 404 may be trained with the inputs from the meal activity component 402, the insulin delivery component 406, stress state component 408 and the CGM sensor 410 until the model component 404 is able to estimate a user's meal glucose pattern. The model component 404 may be used by an automatic glucose control algorithm or application, such as 265 or 222 of FIG. 2, based on one or more of the inputs, such as the given the ingested carbohydrates (in grams), the sequence of blood glucose measurement values prior to the meal, the stress level and the time occurrence of the stress with respect to the time of ingestion of the meal, and the insulin deliveries within the set period of time.

Figure 5A:
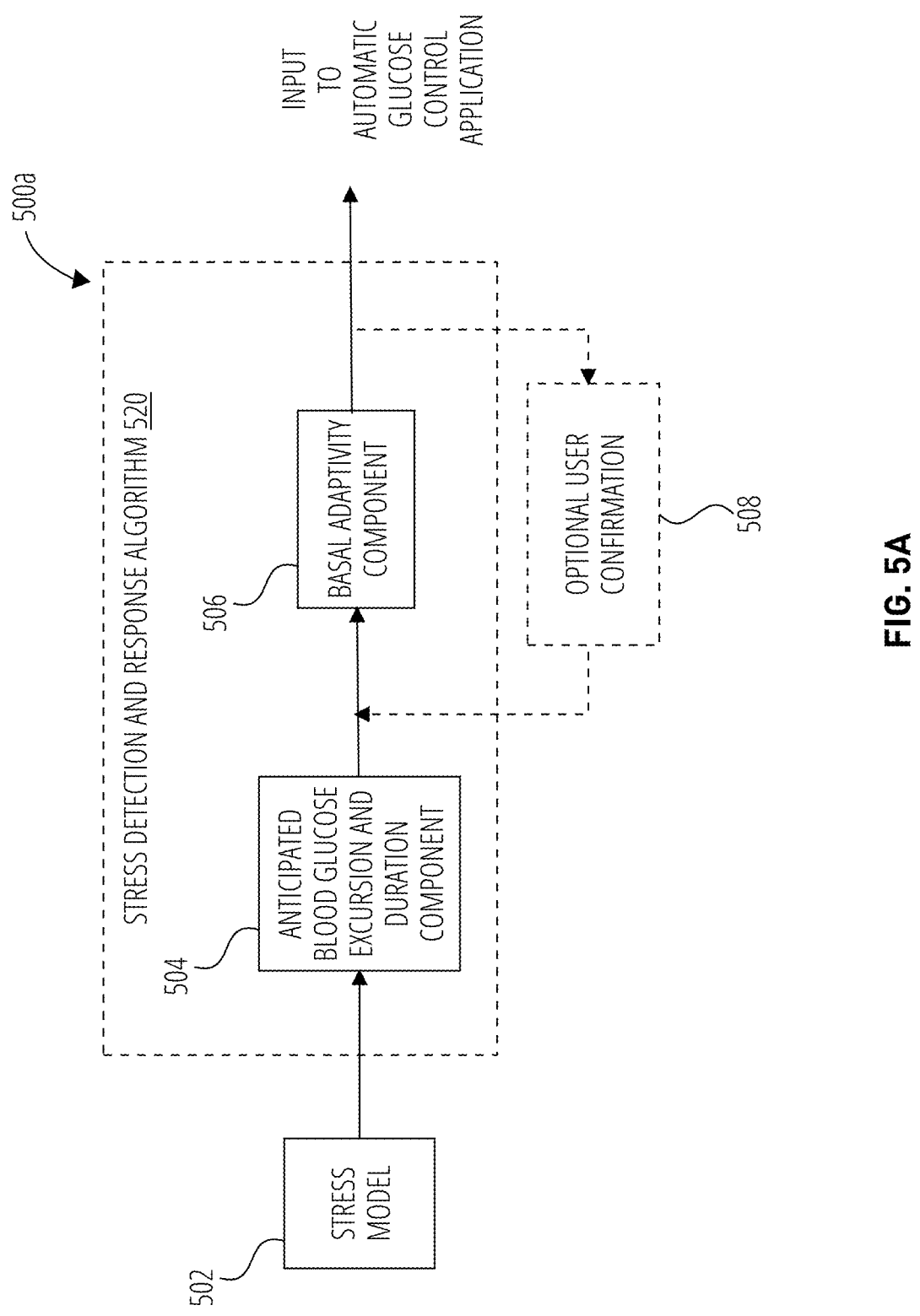
FIG. 5A illustrates an aspect of the subject matter enabling basal adaptivity in response to user experiencing stress in accordance with one embodiment.

FIG. 5A illustrates an aspect of the subject matter enabling basal adaptivity in response to user experiencing stress in accordance with one embodiment. The process 500a may be implemented by stress detection and response algorithm 520 that is operable to provide information to an automatic glucose control application, such as 265 of FIG. 2 to enable adaptations to a user's basal dosages in response to stress. In the example, an automatic glucose control application may determine whether the user's drug treatment plan is to be modified based on the output of process 500a.

The process 500a may encompass inputs from the stress model 502 to the stress detection and response algorithm 520. The stress detection and response algorithm 520 may include an anticipated blood glucose excursion and duration component 504 and a basal adaptivity component 506. The basal adaptivity component 506 may provide inputs to the automatic glucose control application. The basal adaptive component 506 may be a machine learning algorithm that may be utilized to take the input from the stress model and model or replicate the effect on blood glucose excursions. The machine learning model may learn the baseline blood glucose profiles when there is no stress as well as the blood glucose excursions in the presence of various levels of stress. In the case of closed loop systems, excess insulin delivery as compared to baseline insulin delivery may also be modeled.

An increased level of stress is often associated with an elevated blood glucose level, which may last for an extended duration. The process 500a is directed to limiting the rise of the elevated blood glucose level until the level of stress is reduced. The individualized stress model 502 may have been trained, for example, to respond to a user's blood glucose measurement values as well as other inputs as described with reference to other examples and is expected to provide guidance to the automatic glucose control application.

Based on the input from the basal adaptivity component 506 of the stress detection and response algorithm 520, the basal insulin delivery may be adjusted to compensate for the anticipated blood glucose excursion resulting from the stress experienced by the user.

The stress model 502 may operate according to previously described examples and may output a stress level determination for use by the 520. For example, the stress model 502 may indicate to the anticipated blood glucose excursion and duration component 504 of the stress detection and response algorithm 520 that the user is experiencing stress at a stress level of 3. In response to the input of a stress level 3, the anticipated blood glucose excursion and duration component 504 may adjust estimates of the future blood glucose measurement values of the user based on the inputs received from the stress model 502, where the inputs indicate a stress level being experienced by the user. For example, if the stress level is 3, the basal adaptivity component 506 may output a signal corresponding to a recommendation that the basal insulin delivery be increased by 5%, or, if the stress level is 4, the basal adaptivity component 506 may output a signal corresponding to a recommendation that the basal insulin delivery be increased by 10%. As added embodiments of basal adaptivity, the changed basal value may nominally remain in effect for the next 30 minutes. At the end of this time period the new stress level may be used to adapt the basal value from the base nominal value. If the stress has reduced to normal levels, then the basal value may be switched back to baseline. Or, on the other hand, if the stress is even higher, then the basal value may be increased further for the next 30 minutes.

Of course, other recommendations may be provided, such as a specific volume of a liquid drug or combinations of liquid drugs to be delivered. The basal adaptivity component 506 may output the signal for recommended basal insulin delivery as an input to an automatic glucose control application.

The above specific adaptations in basal dosage depend on the individual and may be derived, for example, based on the blood glucose excursion model as described in FIG. 4A. The anticipated blood glucose excursion and duration component 504 may output an adjusted estimate of the user's blood glucose measurement values that may be different from a user's original setting for basal delivery. In an example, once the effects of the increased stress level on the user's blood glucose levels diminish, the processor may return basal drug delivery levels to an original setting of the automatic glucose control application.

The anticipated blood glucose excursion and duration component 504 may be similar to the model component 404 and may be implemented as a machine learning algorithm that may be utilized to take the input from the stress model and model or replicate the effect on blood glucose excursions. Representative machine learning algorithms include recurrent neural network, which is a type of deep neural network well suited for time series modeling with long and short term memory. The anticipated blood glucose excursion and duration component 504 may, for example, learn the baseline blood glucose profiles when there is no stress as well as the blood glucose excursions in the presence of various levels of stress. The specific increases in the blood glucose may be dependent on the specific individual's response to stress but after a period of training, the anticipated blood glucose excursion and duration component 504 may learn the specific individual's response to stress.

For example, the basal insulin may be automatically modulated, or alternatively, the stress detection and response algorithm 520 may suggest a temporary change in the basal level setting which is accepted by the user. As an option, when an adjustment to the basal delivery dosage is determined to be made, the stress detection and response algorithm 520 may be operable to generate a notification of the proposed adjustment. The notification may be presented on a user interface with a prompt requesting user confirmation of the adjustment or user permission to make an adjustment. The stress detection and response algorithm 520 may have settings to proceed either with or without user confirmation or permission received via the optional user confirmation 508.

The process 500a may be implemented by a stress detection and response algorithm, such as stress detection and response algorithm or application 262 of FIG. 2, in combination with inputs and evaluation of data by a stress detection and response algorithm 520.

Figure 5B:
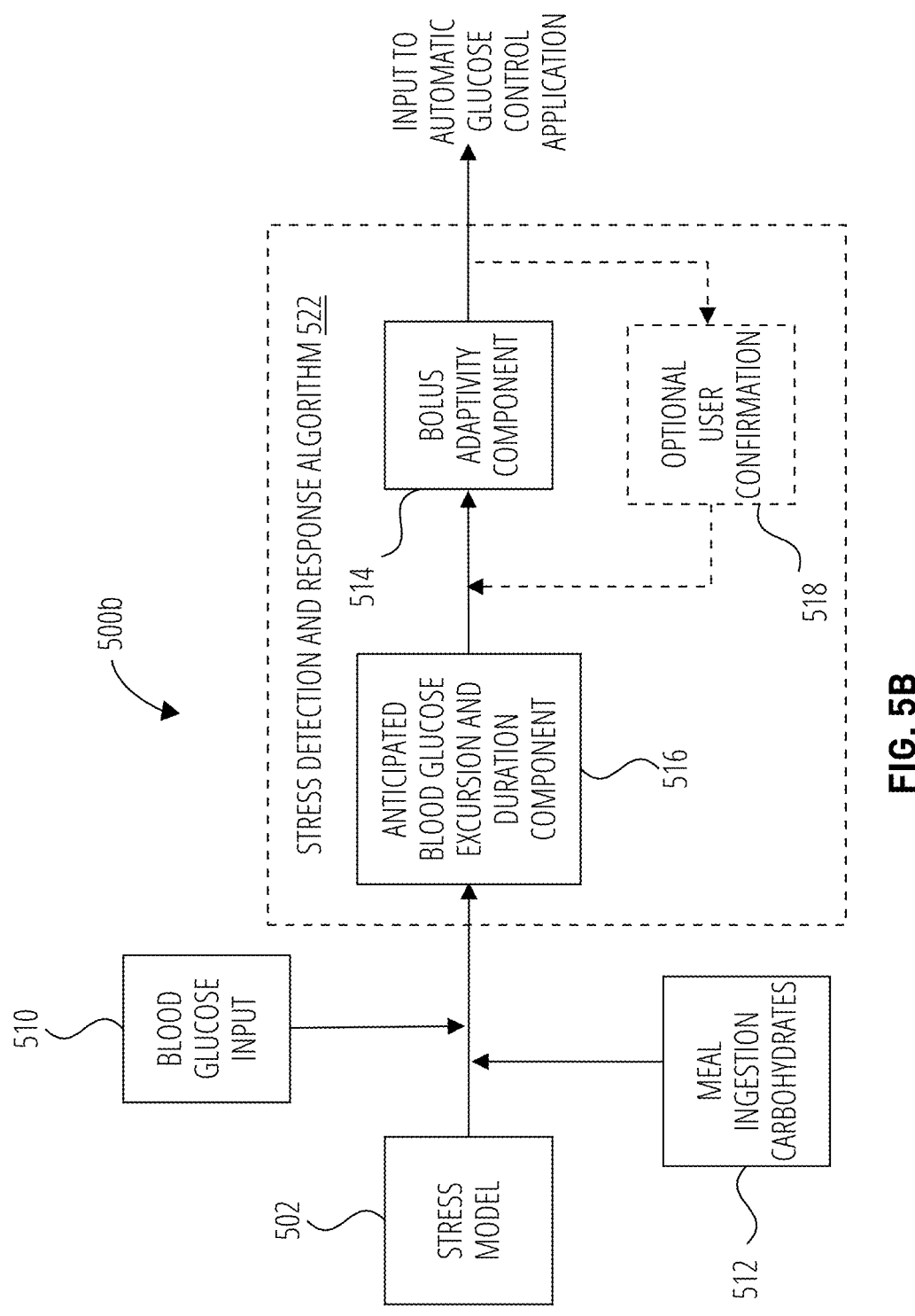
FIG. 5B illustrates an aspect of the subject matter enabling bolus adaptivity in response to user experiencing stress in accordance with one embodiment.

FIG. 5B illustrates an aspect of the subject matter enabling bolus adaptivity in response to user experiencing stress in accordance with one embodiment. The process 500b may be implemented by a stress detection and response algorithm, such as stress detection and response algorithm 522, which provides an input to an automatic glucose control application, such as 310 of FIG. 3. Based on an output from process 500b, the automatic glucose control application may determine whether the user's drug treatment plan is to be modified.

The stress detection and response algorithm 522 may implement the bolus adaptivity recommendation of process 500b. The stress detection and response algorithm 522 may be configured similar to the anticipated blood glucose excursion and duration component 504 but is operable to utilize a bolus adaptivity component 514. In the process 500b, the stress detection and response algorithm 522 may make a recommendation of an amount of insulin to be delivered in a bolus dosage.

The amount of insulin in the bolus dosage may be proportional to the number of grams of carbohydrates and the patient's insulin-to-carbohydrate ratio (ICR) as modulated by the effect of stress. Inputs to the stress detection and response algorithm 522 include an input from a trained stress model 502, a blood glucose input 510 from a CGM sensor, such as 410 of FIG. 4A, and a count, for example, in grams, of meal ingestion carbohydrates 512. The meal ingestion carbohydrates 512 may be an input that is provided by a meal activity component, such as 402 of FIG. 4A, which may be a meal detection and calculation application, a user input related to a meal, a carbohydrate calculator, or the like.

The anticipated blood glucose excursion and duration component 516 may use the blood glucose input 510, the meal ingestion carbohydrates 512, and the output from the stress model 502 to provide guidance on the post prandial blood glucose excursion.

Based on the anticipated blood glucose excursion prediction from the anticipated blood glucose excursion and duration component 516, the bolus adaptivity component 514 may recommend an amount of insulin to be delivered in a bolus dosage. In this example, the event causing the stress may have occurred at the time of meal ingestion or within several minutes after the ingestion of the meal. Based on the user's stress level, blood glucose level, and the amount of carbohydrates the user has ingested, the amount of insulin in the bolus dosage may be modulated.

For example, the bolus adaptivity component 514 may recommend that a bolus be delivered as a gated (wave) bolus, because of an anticipated delayed glucose clearance as well as an elevated blood glucose level that is due to the ingestion of the meal. In one example, in response to an input including the recommendation from bolus adaptivity component 514, an automatic glucose control application may deliver 70% of the bolus dosage upfront and hold 30% of the bolus in reserve to be administered later (e.g., within 30 minutes or the like).

In another example, the usual mealtime bolus as per the carbohydrate requirement may be delivered as well as an additional 10% of the usual mealtime bolus at the time of stress occurrence. Alternatively, when the user's stress level is low enough (e.g., a stress level 0 or 1) not to cause a modification of the bolus dosage, the recommendation from bolus adaptivity component 514 may be to deliver a bolus dosage calculated as the number of grams of carbohydrates divided by the user's insulin-to-carbohydrate ratio.

It has also been noted that stress may reduce the number of carbohydrates ingested and episodes of hypoglycemia has been noted (because the same bolus dosage is delivered but the number of grams of carbohydrates ingested is lower). From this perspective, the stress detection and response algorithm 522 or the automatic glucose control application may maintain a log of the average number of carbohydrates consumed on non-stress days (i.e., days without a stress indication near or at mealtime) and may utilize a model for carbohydrate reduction on stressful days. If such a decrease in the number of carbohydrates ingested is noted, the stress detection and response algorithm 522 may recommend that the automatic glucose control application modulate bolus dosage delivery with respect to the reduced number of carbohydrates. For example, if a reduction in carbohydrates is noted, the stress detection and response algorithm 522 may recommend that the bolus amount be decreased by 5% when the stress level is high. In addition, the bolus dosage may be delivered as a two-part bolus because of the delayed glucose clearance. As an additional specific embodiment, if stress level is high (e.g., Likert scale 4) prior to meal ingestion the stress detection and response algorithm 522 may give a bolus that is a percentage of a typical or expected bolus at meal ingestion, such as a 70% bolus dosage at meal ingestion. The reserved 30% of the bolus dosage may be given assuming the user's carbohydrate pattern does not fall during stress days. Alternatively, if the user is known to reduce carbohydrate consumption on stress days, then the 30% balance bolus dosage may either be forgone or reduced lower, such as to 15% of a bolus dosage. As the system learns the individual patterns of the user, the next refinement by the AGC application may be to lower the nominal initial bolus dosage. An inherent assumption here is that the user may assume they are eating normal meals, but without realizing that they have, in fact, reduced their portions in response to the stress.

The exact strategies and specific numbers may be specific to the individual and may depend on the predictions made by the respective machine learning model for post prandial blood glucose excursion with stress as discussed earlier.

In addition, the user can optionally confirm the bolus recommendation provided by the bolus adaptivity component 514 via an optional user confirmation 518. For example, the stress detection and response algorithm 522 may cause the generation of a prompt or notification related to the bolus recommendation. Based on the response to the prompt or notification, the stress detection and response algorithm 522 may provide or not provide the recommendation to the automatic glucose control application.

FIG. 6 illustrates a flowchart of an example of a process for modifying a liquid drug dosage based on a level of stress experienced by a user of a drug delivery system.

In block 602, a processor executing the process 600 may receive measurement values from the one or more sensors. The one or more sensors includes a skin temperature sensor, a heart rate sensor, a skin conductance sensor, an accelerometer, blood oxygen sensor, or the like.

In block 604, the processor may evaluate each of the received measurement values against a respective threshold measurement value corresponding to the one or more sensors.

In addition, or alternatively, the processor may evaluate the received measurement values from the one or more sensors to determine the user's physical activity state (i.e., the extent of the user's participation in physical activity). Physical activity may cause the generation of sensor signals that may resemble signals generated in response to stress. Therefore, it is advantageous to determine whether a user is participating in physical activity as opposed to experiencing stress.

In addition, inputs from the one or more sensors may be used to identify a physical activity state of a user of the wearable drug delivery system based on the detection of an elevated heart rate of the user, a change in skin conductance of the user, or a change in body temperature of the user. In a specific example, the processor of a wearable drug delivery system may be further operable to receive a skin temperature measurement from the skin temperature sensor. The processor may determine if the skin temperature measurement is lower than an earlier skin temperature measurement provided by the skin temperature sensor. The processor may use the determination that the skin temperature measurement is lower than the earlier skin temperature measure in the determination in block 606 of whether the user is experiencing stress. Similarly, the processor may use the accelerometer signal in the determination in block 606 of whether the user is experiencing stress. In a further example, an attribute of an accelerometer signal received as the input may be used as a marker of physical activity of the user. The accelerometer signal may indicate sudden movements that have previously been classified (for example, based on a user input) as movements corresponding to exercise or physical activity (i.e., jogging, hiking, biking or the like).

When the processor does determine that the user is likely (e.g., a 95% confidence level or the like) participating in physical activity, the processor may output an indication of the user's physical activity state and, in response the stress detection and response algorithm, may exclude a period of time corresponding to the physical activity from the sensor signals.

As in block 606 of FIG. 6, the process 600 includes determining based on a result of the evaluation of each of the received measurement values whether the user is experiencing stress. In the specific example, the processor, in response to the skin temperature measurement being lower than the earlier skin temperature measurement, may generate a signal indicating the user is experiencing stress.

The processor may be operable to estimate the degree of stress in response to the determination the user is experiencing stress (block 608).

In block 610, process 600, based on the degree of stress, caused the processor to modify a pending dosage of the liquid drug to be delivered, a time of delivery of the pending dosage, or both. For example, the pending dosage may be a basal dosage. The basal dosage may temporarily be adjusted until the stress is alleviated based on the determined degree of stress or stress level the user is determined to be experiencing. For example, if the degree of stress is equal to stress level 3 (on a scale of 0-4), the dosage of insulin delivered as basal insulin dosage may be increased by 5% (from a typical zero stress level dosage volume) for the duration of the elevated stress level, or if the degree of stress is equal to stress level 4 (on the scale of 0-4), the dosage of insulin delivered as basal insulin dosage may be increased by 10% (from a typical zero stress level dosage volume) for the duration of the elevated stress level. The automatic glucose control application may increase the volume of the basal dosage as the stress level is determined to increase, so the user may be experiencing a stress level of 3 for a period of time and the basal dosage may be increased as suggested above. Subsequently, the stress detection and response algorithm may determine the user is experiencing stress at a stress level of 4, and the basal dosage may be increased again to volumes as suggested above.

In an example of a pending dosage being a bolus dosage, an automatic glucose control application may deliver 70% of the bolus dosage immediately or at an originally specified time and hold 30% of the bolus dosage in reserve to be administered later (e.g., after or within 30 minutes, or the like). The delayed portion of the bolus dosage may be delivered all at once after the period of time (e.g., 30 minutes), or may be delivered slowly over the period of time (e.g., linearly, such as 1% delivered every minute over 30 minutes, to yield 30% of the original).

In another example, when the processor is modifying the imminent dosage or pending dosage of the liquid drug to be delivered, the time of delivery of the imminent or pending dosage, or both at block 610. The processor may, upon receiving an evaluation of the degree of stress with reference to results of a machine learning algorithm trained using user responses to multiple degrees of stress, determine the modified imminent dosage is at least one of a stress-modified dosage that is an amount of the liquid drug that is different from an amount of the imminent or pending dosage of the liquid drug to be delivered, a first stress-modified delivery time that is different from an imminent delivery time of a next dosage (i.e., a dosage after the modified imminent or pending dosage) of the liquid drug, a combination of the stress-modified dosage and the first stress-modified delivery time, or a combination of the stress-modified dosage and a second stress-modified delivery time, wherein the second stress-modified delivery time is based on the stress-modified dosage and is different from the first stress-modified delivery time.

The modification of the pending dosage or the imminent dosage may, for example, include modifying an amount of a liquid drug to be delivered as a basal dosage via basal delivery, modifying a time for delivery of the basal dosage, modifying a frequency of delivery of a basal dosage, modifying a time of delivery of a bolus dosage that was the imminent dosage of the liquid drug, modifying an amount of a liquid drug to be delivered as a modified bolus dosage via a bolus delivery, or modifying a time of delivery of the modified bolus dosage.

In block 612, the process 600 causes the liquid drug to be expelled from the wearable drug delivery device according to the modified pending dosage, the modified time of delivery of the pending dosage, or both.

Figure 7:
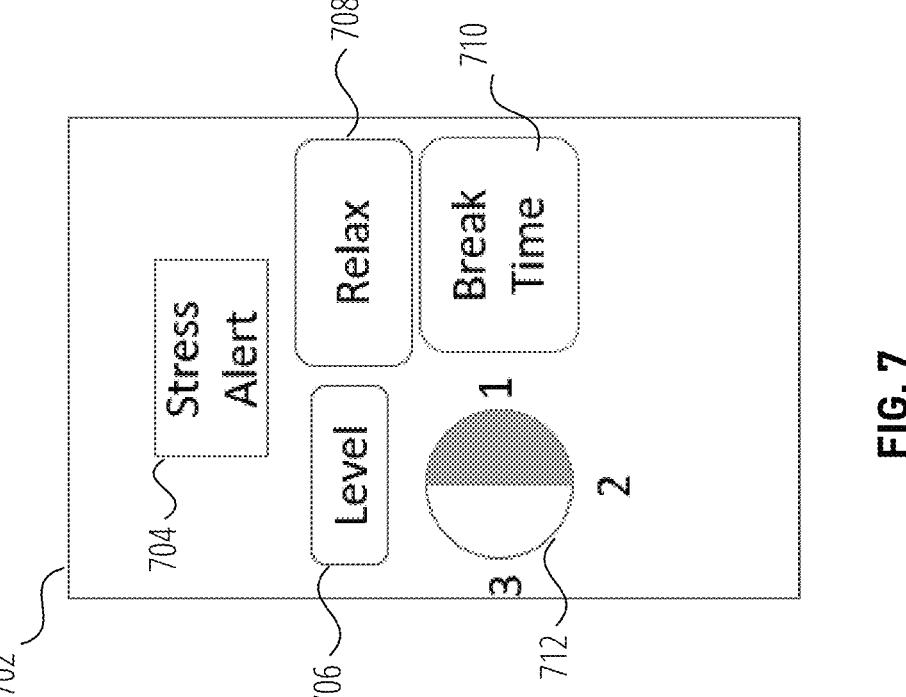
FIG. 7 illustrates an example of a graphical user interface usable with the techniques, processes and systems described herein.

FIG. 7 illustrates an example of a graphical user interface usable with the techniques, processes and systems described herein. The graphical user interface 702 may be presented on a display screen or touchscreen display of a user device, such as controller 260 of FIG. 2 or a display of a smart accessory device, such as 207 of FIG. 2. The alerts, notifications, recommendations, prompts and information may be provided in the graphical user interface 702. A header 706 may indicate the information presented by the dial 712.

Real time stress level tracking may be provided by dial 712, for example, and user interaction can help alert via, for example, alert 704, that a high stress level has been determined for the user by the stress detection and response algorithm. The stress level determined to be experienced by the user may be shown by dial 712. In addition, the real time stress level tracking may be used to improve model performance of the above-described machine learning models, such as model 216 or model 218 of FIG. 2.

In response to detection of stress, an alert may be provided to the user to relax via recommendation 708 and suggest relaxation options, such as relaxation option 710. In this example, the stress level may be indicated by an indicator on dial 712 is a stress level 2 on a stress level scale of 0-4, and the relaxation option 710 suggests that it is "break time" to the user. The stress detection and response algorithm may be operable to factor time of day when making recommendations and presenting relaxation options.

Figure 8:
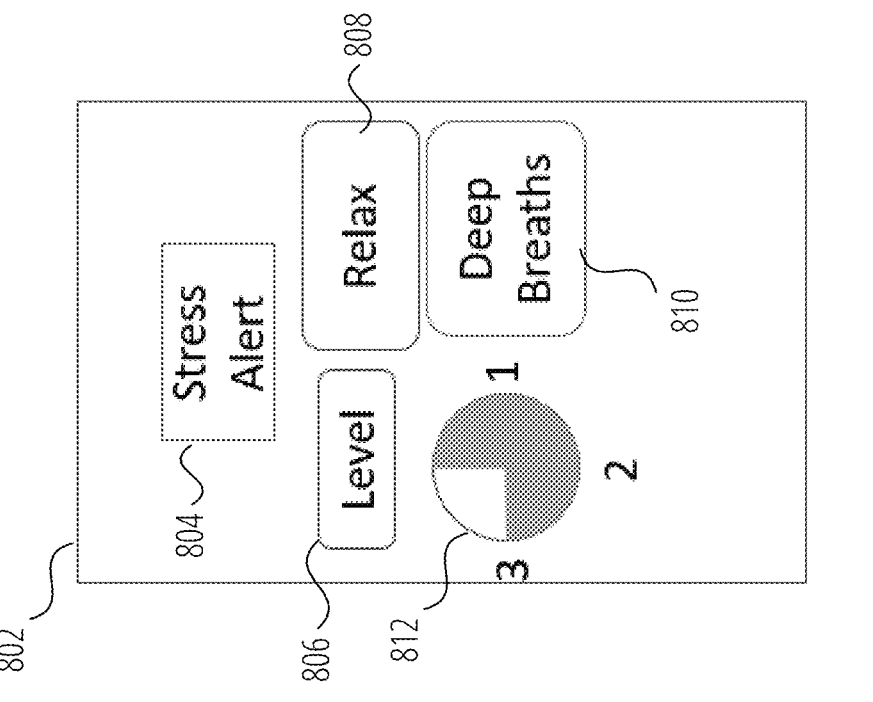
FIG. 8 illustrates another example of a graphical user interface usable with the techniques, processes and systems described herein.

FIG. 8 illustrates another example of a graphical user interface usable with the techniques, processes and systems described in the earlier examples. Similar to the graphical user interface 702, the graphical user interface 802 may also include an alert 804, a header 806, a dial 812, a recommendation 808 and a relaxation option 810. The header 806 may indicate the information presented by the dial 812. In the graphical user interface 802, the user's stress level as shown in dial 812 has increased from the example of FIG. 7. In response to the increased stress level, the stress detection and response algorithm may update the dial 812 to show the stress level and also update the relaxation option 810. In the example, the relaxation option 810 has been changed from "break time" as shown in FIG. 7 to "deep breaths" in response to the increased stress. In addition, the stress detection and response algorithm may be operable to factor in the time of day when making recommendations, such as recommendation 808. For example, during the day, an optional break or walk, deep breathing exercise or the like may be provided as a relaxation option 810.

Figure 9:
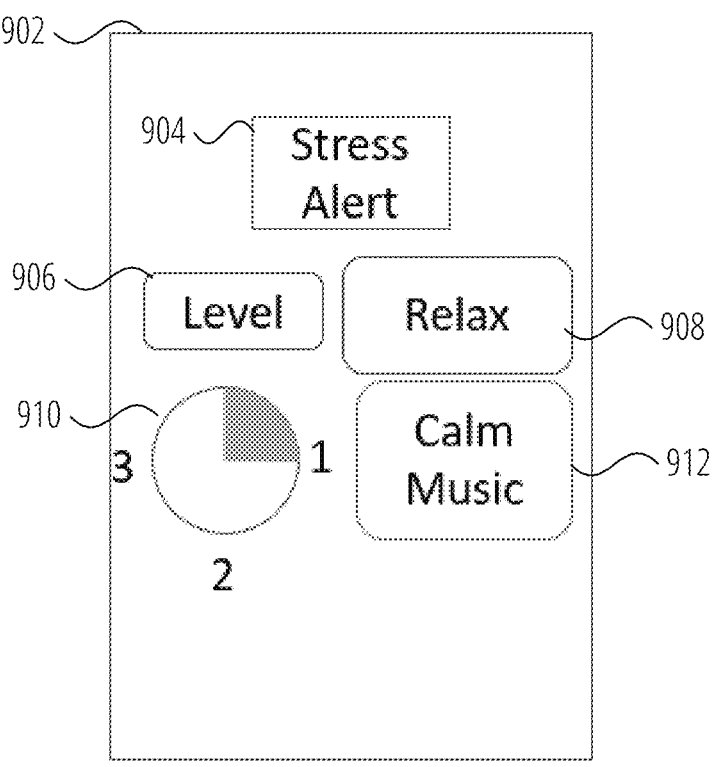
FIG. 9 illustrates yet another example of a graphical user interface usable with the techniques, processes and systems described herein.

FIG. 9 illustrates yet another example of a graphical user interface usable with the techniques, processes and systems described in the earlier examples. Similar to the graphical user interfaces 702 and 802, the graphical user interface 902 may also include an alert 904, a header 906, a dial 910, a recommendation 908 and a relaxation option 810. As mentioned above, the stress detection and response algorithm may be operable to factor time of day when making recommendations. In the example of FIG. 9, the user may be experiencing a minimal amount of stress (stress level 1 as shown by dial 910) at night-time, for example, so the recommendation 908 provided by the stress detection and response algorithm is for the user to relax by using the relaxation option 912, which suggests "calm music."

Figure 10:
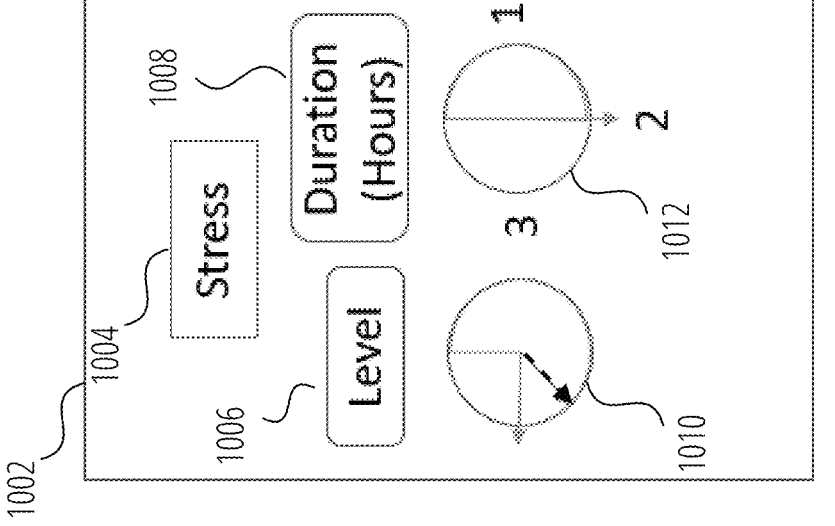
FIG. 10 illustrates a further example of a graphical user interface usable with the techniques, processes and systems described herein.

FIG. 10 illustrates a further example of a graphical user interface usable with the techniques, processes and systems described in the earlier examples. The graphical user interface 1002 may also include an Information indicator 1004, an information identifier 1006, an information category 1008, an information history dial 1010, and information category graphic 1012. The stress detection and response algorithm may store information related to the stress level determinations and enable users to monitor their stress levels as well as tracking their blood glucose time in range, which can help the user to understand their overall stress levels and how it has impacted their blood glucose control. For example, the graphical user interface 1002 may present an information indicator 1004, which in this case may be the stress experienced by the user over a period of time, such as the past 24 hours, 36 hours or the like.

The information indicator 1004 may indicate the information being presented, which in this example is stress, and information identifier 1006 may indicate that the level of stress being presented in the information history dial 1010, while the information category 1008 may indicate the duration of the stress (in this example, 2 hours) during the period of time. The information history dial 1010 may show a maximum level (shown by the upper arrow) and an average level (shown by the dashed arrow). Other categories of information that may be presented include blood glucose level, insulin dosage amounts, an amount of insulin onboard, total carbohydrates consumed, and the like.

Figure 11:
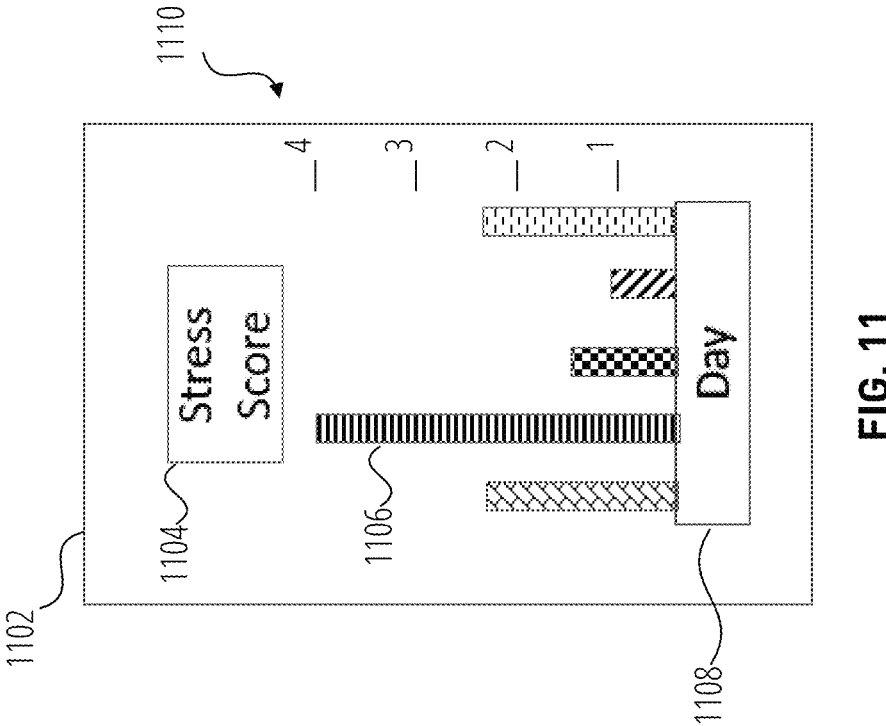
FIG. 11 illustrates yet a further example of a graphical user interface usable with the techniques, processes and systems described herein.

FIG. 11 illustrates yet a further example of a graphical user interface usable with the techniques, processes and systems described in the earlier examples. Stress level tracking in the form of average score per day, hourly scores, the number of high stress days (e.g., where high stress means when the stress level was equal to 4) in a month, and the like can be shown to the user to let them understand their stress level fluctuations. For example, the graphical user interface 1102 may include the information indicator 1104, which indicates the user's stress score. In the example of FIG. 11, the stress score is the user's daily score as indicated by the time header 1108, which indicates "Day." Of course, other time frames besides "Day," such as hours, daytime, afternoon, weeks or months may be presented. The stress level for each day may be indicated by the daily score graphic 1106 that may be measured against the stress level index 1110.

Other information may also be presented blood glucose level, insulin dosage amounts, an amount of insulin onboard, total carbohydrates consumed, and the like.

Figures 12A, 12B:
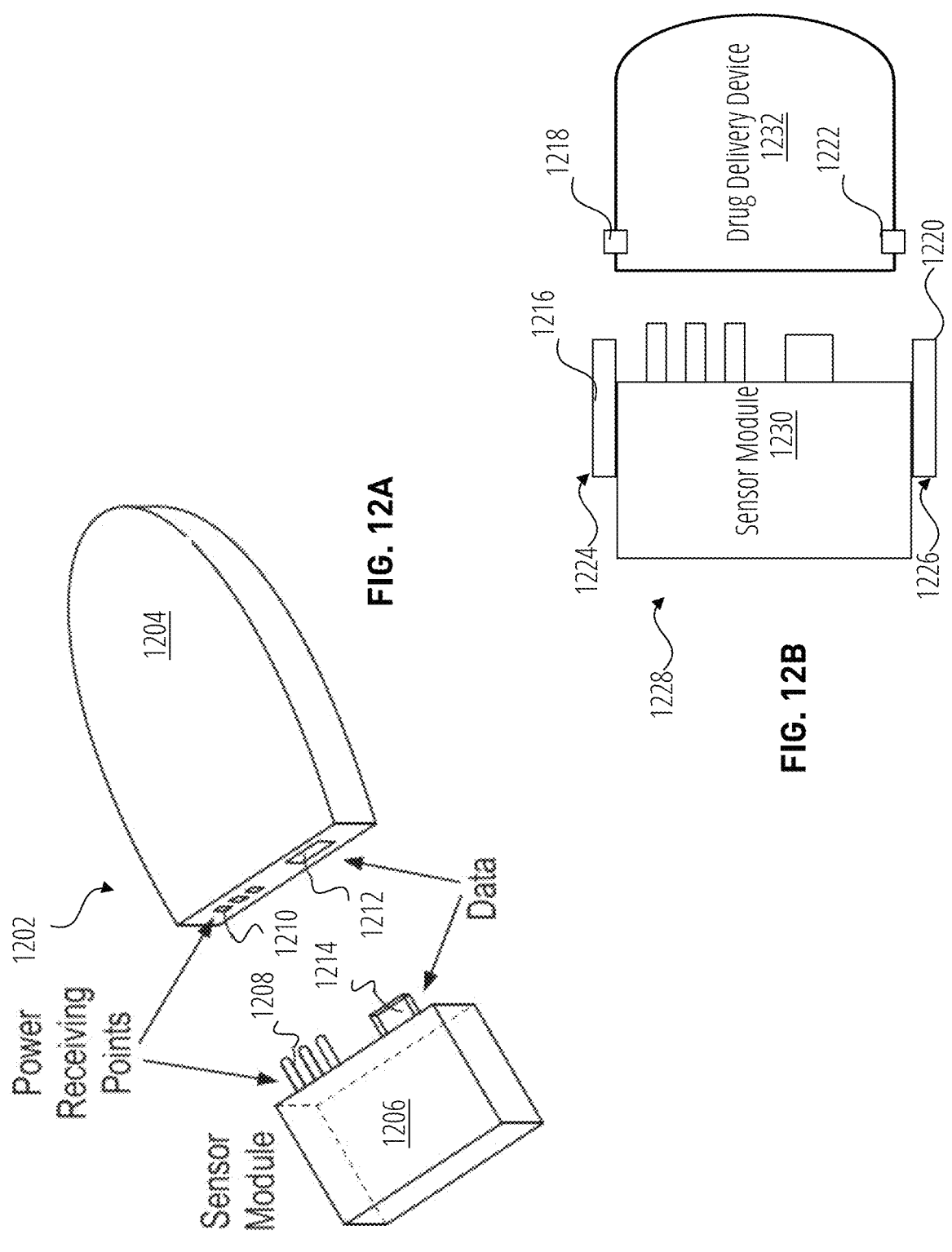
FIG. 12A illustrates an isometric view of an example of a drug delivery system including a sensor module and a drug delivery device.
FIG. 12B illustrates a top view of another example of the drug delivery system in accordance with another aspect of the disclosed subject matter.

FIG. 12A illustrates an isometric view of an example of a drug delivery system including a sensor module 1206 and a drug delivery device 1204. The drug delivery system 1202 may include a drug delivery device 1204 and a sensor module 1206.

The sensor module 1206 may include power receiving contacts 1208 and a data transfer connection 1214. The drug delivery device 1204 may include power contacts 1210 and data connection 1212. The power receiving contacts 1208 of the sensor module 1206 may connect to the power contacts 1210 via a snap fit, compression fit or the like. Similarly, the data transfer connection 1214 may couple to the data connection 1212 via a snap fit, compression fit, or the like. The data transfer connection 1214 may be a connector such as universal serial bus (USB) connector, a micro-USB connector or the like.

When the sensor module 1206 is coupled to the drug delivery device 1204, power may be delivered to the sensor module 1206 via the connection of the power receiving contacts 1208 to the power contacts 1210. The sensor module 1206 may include a number of different sensors that may be operable to detect different conditions or physical attributes of a user of the drug delivery system 1202 as described according to earlier examples.

FIG. 12B illustrates a top view of another example of the drug delivery system in accordance with another aspect of the disclosed subject matter. The drug delivery system 1228 includes sensor module 1230 and drug delivery device 1232.

The sensor module 1230 includes a clip 1216, a clip attachment 1218, a clip 1220, a clip attachment 1222, a release point 1224, a release point 1226, and a drug delivery system 1228.

In the example of FIG. 12B, the clip 1216 and clip 1220 are operable to engage clip attachment 1218 and clip attachment 1222, respectively. The clips 1216 and 1220 may snap fit to the clip attachments 1218 and 122 and thereby secure the sensor module 1230 in place against the drug delivery device 1232. The sensor module 1230 may be released from the drug delivery device 1232 by "unclipping" or unfastening the clips 1216 and 1220 from their respective clip attachments 1218 and 1222. For example, a user may engage both the release point 1224 of clip 1216 and the release point 1226 of clip 1220, which may cause, respectively, the end of the clip 1216 opposite from the release point 1224 to disengage from the clip attachment 1218 as well as engage end of the clip 1220 opposite from the release point 126 to disengage from the clip attachment 1222. With the clips 1216 and 120 disengaged sensor module 1230 may be uncoupled from the drug delivery device 1232.

While the clips 1216 and 120 and their clip attachments 1218 and 1222 are shown other forms of snap fittings may be used to secure the sensor module 1230 to the drug delivery device 1232.

Figure 13:
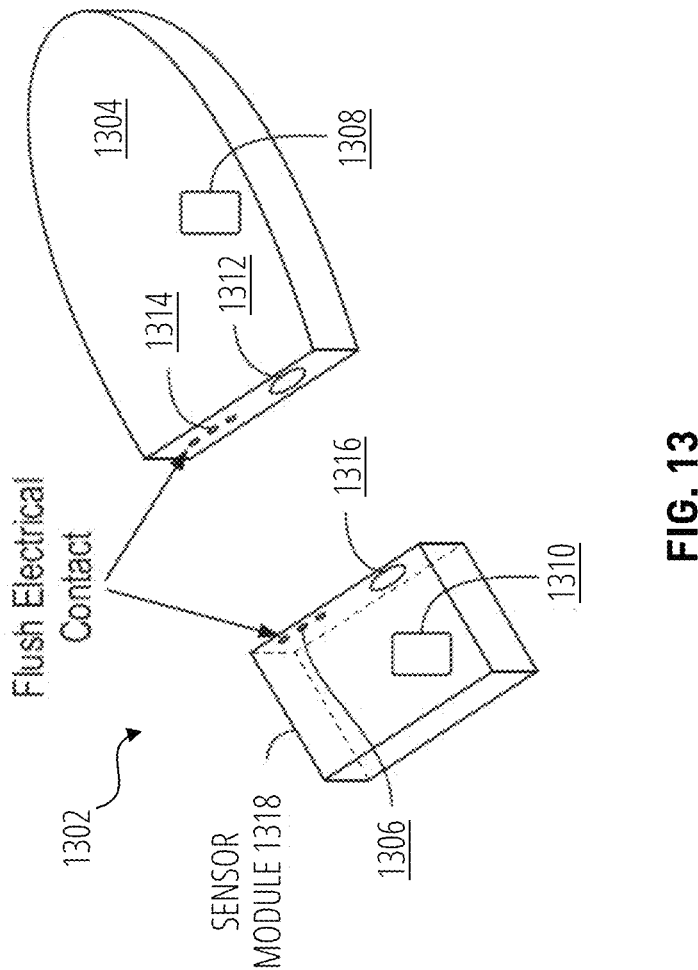
FIG. 13 illustrates an isometric view of another example drug delivery system including a sensor module and a drug delivery device.

Another example of securing a sensor module to a drug delivery device may include magnetic attachment. FIG. 13 illustrates an isometric view of another example drug delivery system including a sensor module and a drug delivery device. In the example drug delivery system 1302, a sensor module 1318 may be operable to magnetically couple to the drug delivery device 1304. The sensor module 1318 may include electrical contacts 1306, a magnet 1316 and a communication device 1310, which enables a wireless data connection, such as via a Bluetooth® connection, or the like. The drug delivery device 1304 may include electrical power contacts 1314, a magnet 1312 and a communication device 1308. The electrical power contacts 1314 may be flush with an external surface of the drug delivery device 1304 and the electrical contacts 1306 may be flush with an external surface of the sensor module 1318. The sensor module 1318 and the drug delivery device 1304 may be operable to couple to one another via the magnets 1316 and 1312. The magnet 1312 of the drug delivery device 1304 may maintain contact with magnet 1316 of the sensor module 1318, which draws the electrical contacts 1306 into alignment and electrical contact with electrical power contacts 1314. Data from the sensor module 1318 may be transferred via the communication device 1310 to the drug delivery device 1304, which receives the transferred data via the communication device 1308.

Figure 14:
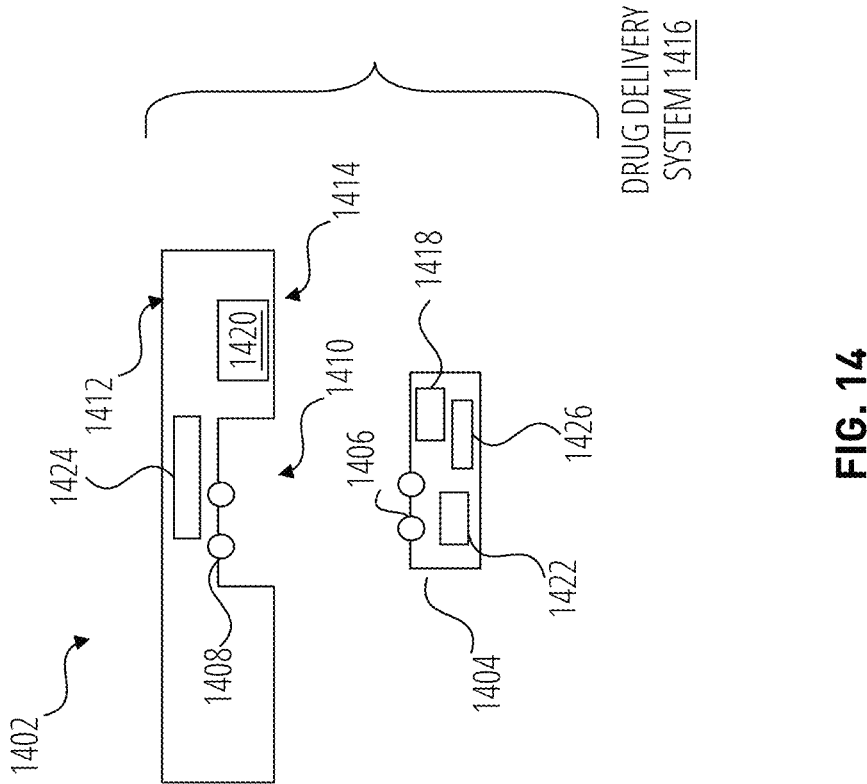
FIG. 14 illustrates a cross-sectional view of another example of a drug delivery system including a sensor module and a drug delivery device.

FIG. 14 illustrates a cross-sectional view of another example of drug delivery system. The drug delivery system 1416 including a sensor module 1404 and a drug delivery device 1402.

In the example, the drug delivery device 1402 may include delivery device communication circuitry 1420, power contacts 1408, and a magnet 1424. The drug delivery device may include a top surface 1412, a bottom surface 1414, and a module opening 1410. The module opening 1410 in the bottom surface 1414 is operable to hold the sensor module 1404. The sensor module 1404 may include electrical contacts 1406, magnet 1418, sensor communication circuitry 1422 as well as sensors 1426, which may include an Accelerometer, a Gyroscope, a skin conductance detector, a skin temperature sensor, an analyte sensor, a heart rate monitor, blood oxygen sensor, the sensors described above with respect to earlier examples, and the like. Note the respective individual sensors may be separate within the sensor module 1404 but are collectively referred to as sensors 1426.

The magnet 1418 of sensor module 1404 may magnetically couple to Magnet 1424 of the drug delivery system 1402 and secure the sensor module 1404 in the module opening 1410. The sensor module 1404 when held in the module opening 1410 contacts the surface to detect physical attributes, such as heart rate, blood oxygen saturation, perspiration, and other attributes. In addition, the sensors 1426 of the sensor module 1404 may be operable to measure movements of the user using sensors, such as the accelerometer, gyroscope and the like as well as physiological conditions of the user as described above with reference to the earlier examples.

The sensor module 1404 may electrically connect via electrical contacts 1406 to the power contacts 1408 of the drug delivery device 1402 to obtain power. The data generated from the measurements made by the sensors in the sensor module 1404 may be transferred via a wireless communication link established by a pairing protocol between the sensor communication circuitry 1422 of the sensor module 1404 and the delivery device communication circuitry 1420 of the drug delivery device 1402. For example, the data related to the physiological conditions and movements of the user made by the sensors 1426 of the sensor module 1404 may be wirelessly transferred to the drug delivery device 1402, which may process the received data as described with reference to other examples.

Other technical features may be readily apparent to one skilled in the art from the following figures, descriptions, and claims.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:
1. A wearable drug delivery system, comprising:
one or more sensors operable to measure a physiological condition of a user;
a processor communicatively coupled to the one or more sensors;

a pump mechanism coupled to the processor and to a drug container, wherein the drug container is operable to store a liquid drug;
a memory coupled to the processor, the memory including programming code;
the processor, when executing the programming code, operable to:
receive measurement values from the one or more sensors;
evaluate each of the received measurement values against a respective threshold measurement value corresponding to the one or more sensors;
determine based on a result of the evaluation of each of the received measurement values whether the user is experiencing stress;
in response to the determination the user is experiencing stress, estimate a degree of stress;
based on the degree of stress, modify a pending dosage of a liquid drug to be delivered, a time of delivery of the pending dosage, or both; and
expel the liquid drug according to the modified pending dosage, the modified time of delivery of the pending dosage, or both.

2. The wearable drug delivery system of claim 1, wherein the one or more sensors includes a skin temperature sensor, a heart rate sensor, a skin conductance sensor, or an accelerometer.

3. The wearable drug delivery system of claim 2, wherein the processor, prior to evaluating each of the received measurement values against the respective threshold measurement value corresponding to the one or more sensors, is further configured to:
identify a physical activity state based on detection of an elevated heart rate of the user, a change in skin conductance of the user, or a change in body temperature of the user.

4. The wearable drug delivery system of claim 3, wherein the processor is further operable to:
in response to the physical activity state indicating participation in physical activity by the user, exclude a period of time corresponding to the physical activity state from the determination of whether the user is experiencing stress.

5. The wearable drug delivery system of claim 2, wherein prior to evaluating each of the received measurement values against a respective threshold measurement value corresponding to the one or more sensors, the processor is operable to:
determine a physical activity state of the user based on an input from the accelerometer, wherein an attribute of an accelerometer signal received as the input is used as a marker of physical activity of the user.

6. The wearable drug delivery system of claim 5, wherein the processor is further operable to:
in response to the physical activity state indicating participation in physical activity by the user, exclude a period of time corresponding to the physical activity state from evaluation for stress.

7. The wearable drug delivery system of claim 2, wherein evaluating each of the received measurement values against the respective threshold measurement value corresponding to the one or more sensors, the processor is further operable to:
determine if a skin temperature measurement received from the skin temperature sensor is lower than an earlier skin temperature measurement; and in response to the skin temperature measurement being lower than the earlier skin temperature measurement, generate a signal indicating that the skin temperature measurement is lower than the earlier skin temperature measurement and a number of degrees lower.

8. The wearable drug delivery system of claim 2, wherein the processor is further operable to:

receive the measurement values from the skin temperature sensor by sampling the skin temperature measurement output by the skin temperature sensor at a high frequency to obtain a plurality of skin temperature measurements;

determine a minimum skin temperature measurement from among the plurality of skin temperature measurements;

determine a maximum skin temperature measurement from among the plurality of skin temperature measurements;

determine a standard deviation of the plurality of skin temperature measurements; and use the determined minimum skin temperature, the determined maximum skin temperature, and the determined standard deviation when estimating the degree of stress.

9. The wearable drug delivery system of claim 1, wherein the processor is further operable to:

in response to receiving the inputs from a respective sensor of the one or more sensors, select a group level model from a plurality of group level models, wherein each respective group level model of the group level models enables modeling an individual stress load of a person; and in response to applying the inputs to the selected group level model, generate an individualized stress load model for the user.

10. The wearable drug delivery system of claim 9, wherein the processor, when determining whether the user is experiencing stress, is further operable to:

apply inputs to the individualized stress load model;

process an output for the individualized stress load model to determine whether the user is experiencing stress; and in response to a determination that the user experiencing stress, process the output to provide the estimated degree of stress.

11. The wearable drug delivery system of claim 10, wherein the processor when modifying the pending dosage is operable to:

modify an amount of a liquid drug to be delivered as a basal dosage via basal delivery, modify a time for delivery of the basal dosage, modify an amount of a liquid drug to be delivered as a bolus dosage via a bolus delivery, modify a frequency of delivery of a basal dosage, or modify a time of delivery the bolus dosage.

12. The wearable drug delivery system of claim 9, wherein the processor is further operable to:

use based on an output from the individualized stress load model in the estimating of the degree of stress the user is experiencing; and in response to a determination of the degree of stress the user is experiencing, modifying a drug delivery treatment plan.

13. The wearable drug delivery system of claim 1, wherein the processor, when receiving measurement values from the one or more sensors is operable to:

receive a measure heart rate variability;

compare the measured heart rate variability to a heart rate variability threshold; and in response to the measured heart rate variability exceeding the heart rate variability threshold, generate an indication that the user is experiencing stress.

14. A method comprising:

obtaining a respective measurement value from one or more sensors, wherein each sensor of the one or more sensors obtains data related to a physiological condition of a user;

evaluating each obtained respective measurement value against a respective threshold measurement value corresponding to the one or more sensors;

determining, based on a result of the evaluation of each of the obtained respective measurement values, a degree of stress the user is experiencing;

in response to a determination of the degree of stress the user is experiencing, modifying an imminent dosage of a liquid drug to be delivered, a time of delivery of the imminent dosage, or both; and expelling the liquid drug according to the modified imminent dosage, the modified time of delivery of the imminent dosage, or both.

15. The method of claim 14, wherein modifying the imminent dosage of the liquid drug to be delivered, the time of delivery of the imminent dosage, or both, further comprises:

evaluating the degree of stress with reference to results of a machine learning algorithm trained using user responses to multiple degrees of stress; and determining, based on a result of the evaluating, at least one of:

a stress-modified dosage that is an amount of the liquid drug that is different from an amount of the imminent dosage of the liquid drug to be delivered, or a first stress-modified delivery time that is different from an imminent delivery time of a next dosage of the liquid drug, or a combination of the stress-modified dosage and the first stress-modified delivery time, or a combination of the stress-modified dosage and a second stress-modified delivery time, wherein the second stress-modified delivery time is based on the stress-modified dosage and is different from the first stress-modified delivery time.

16. The method of claim 14, wherein modifying an imminent dosage of the liquid drug to be delivered, a time of delivery of the imminent dosage, or both, further comprises:

modifying an amount of a liquid drug to be delivered as a basal dosage via basal delivery, modifying a time for delivery of the basal dosage, modifying a frequency of delivery of a basal dosage, modifying a time of delivery of a bolus dosage that was the imminent dosage of the liquid drug, modifying an amount of a liquid drug to be delivered as a modified bolus dosage via a bolus delivery, or modifying a time of delivery of the modified bolus dosage.

17. The method of claim 16, wherein evaluating each obtained respective measurement value against the respective threshold measurement value corresponding to the one or more sensors further comprises:

comparing a measured heart rate variability signal obtained from a heart rate sensor to a heart rate variability threshold; and in response to the measured heart rate variability exceeding the heart rate variability threshold, generate an indication that the user is experiencing stress.

18. The method of claim 14, wherein obtaining a respective measurement value from the one or more sensors, wherein each sensor of the one or more sensors obtains data related to a physiological condition of the user, further comprises:

obtaining a measure of heart rate variability.

19. The method of claim 18, further comprising:

evaluating the respective measurement of the heart rate variability by comparing the measured heart rate variability to a heart rate variability threshold; and in response to the measured heart rate variability exceeding the heart rate variability threshold, using a result of the comparing when estimating the degree of stress, the user is experiencing.

20. A non-transitory computer-readable storage medium, the computer-readable storage medium including instructions that when executed by a processor, cause the processor to:

obtain a respective measurement value from one or more sensors, wherein each sensor of the one or more sensors obtains data related to a physiological condition of a user;

evaluate each obtained respective measurement value against a respective threshold measurement value corresponding to the one or more sensors;

determine based on a result of the evaluation of each of the obtained respective measurement values a degree of stress the user is experiencing;

in response to the determination of the degree of stress the user is experiencing, modify an imminent dosage of a liquid drug to be delivered, a time of delivery of the imminent dosage, or both; and cause the liquid drug to be expelled according to the modified imminent dosage, the modified time of delivery of the imminent dosage, or both.

* * * * *